(12) United States Patent
Ogata

(10) Patent No.: US 11,325,933 B2
(45) Date of Patent: May 10, 2022

(54) CATIONIC RUTHENIUM COMPLEX, AND PRODUCTION METHOD THEREFOR AND USE THEREOF

(71) Applicant: Takasago International Corporation, Tokyo (JP)

(72) Inventor: Osamu Ogata, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 378 days.

(21) Appl. No.: 16/499,823

(22) PCT Filed: Mar. 30, 2018

(86) PCT No.: PCT/JP2018/013542
§ 371 (c)(1),
(2) Date: Sep. 30, 2019

(87) PCT Pub. No.: WO2018/181865
PCT Pub. Date: Oct. 4, 2018

(65) Prior Publication Data
US 2020/0102336 A1  Apr. 2, 2020

(30) Foreign Application Priority Data
Mar. 31, 2017  (JP) .............................. JP2017-069797

(51) Int. Cl.
*C07F 15/00* (2006.01)
*B01J 31/16* (2006.01)

(52) U.S. Cl.
CPC ....... *C07F 15/0046* (2013.01); *B01J 31/1616* (2013.01)

(58) Field of Classification Search
CPC ..... C07F 15/008; B01J 31/16; B01J 2231/641
See application file for complete search history.

(56) References Cited

U.S. PATENT DOCUMENTS

2011/0237814 A1  9/2011  Kuriyama et al.
2016/0009632 A1  1/2016  Ogata et al.
2016/0326202 A1  11/2016  Morris et al.

FOREIGN PATENT DOCUMENTS

WO  2012/144650 A1  10/2012

OTHER PUBLICATIONS

English translation of International Preliminary Report on Patentability (IPRP) Chapter 1, issued in correspondiing PCT Application No. PCT/JP2018/013542 dated Oct. 10, 2019.
Rozenel, S., et al., "Bimetallic Ruthenium PNP Pincer Complex as a Platform to Model Proposed Intermediates in Dinitrogen Reduction to Ammonia" Inorganic Chemistry, 2012, Vo.. 51, No. 18, p. 9730-9739.
Tan, Xuefeng et al., Highly Efficient Tetradentate Ruthenium Catalyst for Ester Reduction: Especially for Hydrogenation of Fatty Acid Esters, Organic Letters, 2015, vol. 17, No. 3, p. 454-457.
Kuriyama, Wataru et al., Catalytic Hydrogenation of Esters. Development of an Efficient Catalyst and Processes for Synthesising (R)-1, 2-Propanediol and 2-(1-Menthoxy) Ethanol, Organic Process Research & Development, 2012, vol. 16, No. 1, p. 166-171.
Bianchini, Claudio, et al., "Designing Homogeneous Catalysts, Ru(II) Complexes with Polydentate Mixed-P,N-Donor Ligands", Gazzetta Chimica Italiana, 1992, vol. 122, No. 11, p. 461-470.

*Primary Examiner* — Caixia Lu
(74) *Attorney, Agent, or Firm* — Mintz Levin Cohn Ferris Glovsky and Popeo, P.C.; Peter F. Corless

(57) ABSTRACT

The present invention provides a novel cationic ruthenium complex which is easy to produce and handle and can be procured at a relatively low cost and a production method for the ruthenium complex, a method for producing an alcohol or the like using the ruthenium complex as a catalyst, a method for producing a carbonyl compound using the ruthenium complex as a catalyst, and a method for producing a N-alkylamine compound using the ruthenium complex as a catalyst. The present invention pertains to a ruthenium complex represented by general formula (1): [RuX(CO)$_2$(PNP)]Y (wherein, X represents a monovalent anionic monodentate ligand, Y represents a counter anion, PNP represents a tridentate ligand, and CO represents carbon monoxide), a production method for the ruthenium complex, a catalyst containing the ruthenium complex, and a production method for various organic compounds using the catalyst.

5 Claims, 1 Drawing Sheet

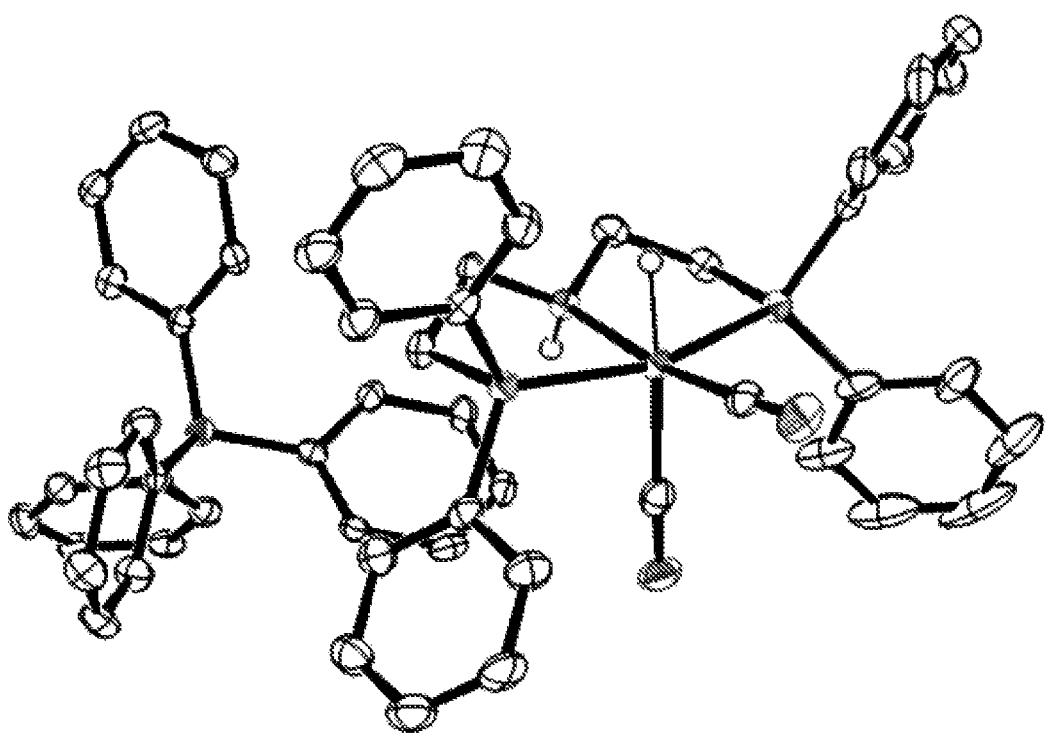

CATIONIC RUTHENIUM COMPLEX, AND PRODUCTION METHOD THEREFOR AND USE THEREOF

CROSS-REFERENCES TO RELATED APPLICATIONS

This application is a 35 U.S.C. § 371 U.S. national entry of International Application PCT/JP2018/013542, having an International filing date of Mar. 30, 2018, which claims under 35 U.S.C. § 119 the benefit of Japanese Patent Application 2017-069797 filed on Mar. 31, 2017. The entire contents of these applications are incorporated herein by reference in their entirety.

TECHNICAL FIELD

The present invention relates to a cationic ruthenium complex and a method for producing the same, and a use of the complex as a catalyst.

BACKGROUND ART

Today, various transition metal complexes composed of transition metals and ligands are used in various reactions as a catalyst in an organic synthesis reaction.

For example, a ruthenium complex having one bis(phosphinoalkyl)amine as a tridentate ligand and one carbon monoxide as a monodentate ligand, has been reported, as a ruthenium complex used in hydrogenation of ketones, esters, and the like (see Patent Document 1). Further, dehydrogenation of alcohols and N-alkylation via condensation of alcohols and amines, using the ruthenium complex as a catalyst have also been reported (see Patent Documents 2 and 3). Meanwhile, a ruthenium complex having one bis(phosphinoalkyl)amine as a tridentate ligand and two carbon monoxides as a monodentate ligand, has been reported, but the ruthenium complex is not used as a catalyst (see Non-Patent Document 1).

CITATION LIST

Patent Document

Patent Document 1: WO 2011/048727
Patent Document 2: WO 2012/144650
Patent Document 3: WO 2014/136374
Non-Patent Document 1: Inorg. Chem. 2012, 51, 9730

SUMMARY OF THE INVENTION

Problems to be Solved by the Invention

An object of the invention is to provide a cationic ruthenium complex which can be produced at a low cost and is easy to handle and a method for producing the same, and a method for producing alcohols by hydrogenation of aldehydes or ketones using the ruthenium complex as a catalyst; a method for producing alcohols, aldehydes or hemiacetals by hydrogenation of esters; a method for producing carbonyl compounds by oxidation of alcohols, hemiacetals or hemiaminals; and a method for producing an N-alkylamine by N-alkylation via condensation of alcohols and amines. These reactions require a novel complex showing high catalytic activity under a milder reaction conditions, in industrial practice from a viewpoint of costs, residual metal problems and a safety issue.

Means for Solving the Problems

The present inventors made extensive investigations considering the above circumstances, and as a result, found a cationic ruthenium complex characterized by having one bis(phosphinoalkyl)amine as a tridentate ligand and two carbon monoxides as a monodentate ligand. It was found that the cationic ruthenium complex found by the present invention is stable powder in the air and thus, is easy to handle, in addition to being capable of being produced at low costs, and is useful as a catalyst of hydrogenation of aldehydes, ketones and esters, dehydrogenation of alcohols, hemiacetals and hemiaminals and an N-alkylation via condensation of alcohols and amines. Based on the findings, the present invention has been completed.

The present invention provides the following [1] to [17].

[1] A ruthenium complex having the following formula (1):

wherein in the formula (1), X represents a monovalent anionic monodentate ligand, Y represents a counter anion and PNP represents a tridentate ligand having the following formula (2):

[Chem. 1]

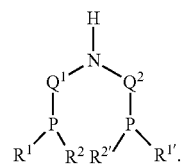

wherein in the formula (2), $R^1$, $R^2$, $R^{1'}$ and $R^{2'}$ each independently represent an alkyl group, an aryl group, an aralkyl group, an alkenyl group, an alkynyl group, an alkoxy group, an aryloxy group, an aralkyloxy group, a heterocyclic group or an amino group, and among the groups, an alkyl group, an aryl group, an aralkyl group, an alkenyl group, an alkynyl group, an alkoxy group, an aryloxy group, an aralkyloxy group and a heterocyclic group may have substituent(s); $R^1$ and $R^2$, and $R^{1'}$ and $R^{2'}$ each independently may bind to each other to form a ring with the adjacent phosphorus atom; $Q^1$ and $Q^2$, each independently represent an optionally substituted alkanediyl group or an optionally substituted aralkylene group; and
CO represents carbon monoxide.

[2] The ruthenium complex of [1], wherein X represents a hydride.
[3] The ruthenium complex of [1] or [2], wherein PNP represents a tridentate ligand having the following formula (3):

[Chem. 2]

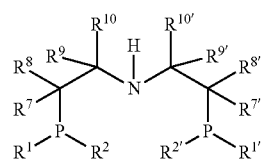

wherein in the formula (3), $R^1$, $R^2$, $R^{1'}$ and $R^{2'}$ are the groups as defined above for the formula (2), $R^7$, $R^{7'}$, $R^8$, $R^{8'}$, $R^9$, $R^{9\prime}$, $R^{10}$ and $R^{10\prime}$ each independently represent a hydrogen atom, an alkyl group, an aryl group, an aralkyl group, an alkenyl group, an alkynyl group, an alkoxy group, an aryloxy group, an aralkyloxy group, a heterocyclic group or an amino group, and among the groups, an alkyl group, an aryl group, an aralkyl group, an alkenyl group, an alkynyl group, an alkoxy group, an aryloxy group, an aralkyloxy group, and a heterocyclic group may have substituent(s); and $R^7$ and $R^8$ or $R^9$ or $R^{10}$, $R^{7\prime}$ and $R^{8\prime}$ or $R^{9\prime}$ or $R^{10\prime}$, $R^8$ and $R^9$ or $R^{10}$, $R^{8\prime}$ and $R^{9\prime}$ or $R^{10\prime}$, $R^9$ and $R^{10}$ or $R^{9\prime}$ or $R^{10\prime}$, $R^{9\prime}$ and $R^{10}$ or $R^{10\prime}$ and $R^{10}$ and $R^{10\prime}$ each independently may bind to each other to form a ring with the adjacent carbon atom(s).

[4] The ruthenium complex of any one of [1] to [3], wherein PNP represents a tridentate ligand having the following formula (4):

[Chem. 3]

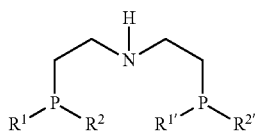

(4)

wherein in the formula (4), $R^1$, $R^2$, $R^{1\prime}$ and $R^{2\prime}$ are the groups as defined above for the formula (2).

[5] The ruthenium complex of [4], wherein $R^1$, $R^2$, $R^{1\prime}$ and $R^{2\prime}$ each independently represents an optionally substituted alkyl group or an optionally substituted aryl group.

[6] A method for producing the ruthenium complex of any one of [1] to [5], comprising reacting a ruthenium complex having the following formula (5) with a primary alcohol and/or carbon monoxide:

$$[RuX^1X^2(PNP)]_q \qquad (5)$$

wherein in the formula (5), $X^1$ and $X^2$ each independently represent a monovalent anionic monodentate ligand, PNP represents the tridentate ligand having the formula (2), (3) or (4), and q represents an integer of 1 or 2.

[7] A method for producing the ruthenium complex of any one of [1] to [5], comprising reacting a ruthenium complex having the following formula (6) with a primary alcohol and/or carbon monoxide:

$$RuX^3X^4(CO)(PNP) \qquad (6)$$

wherein in the formula (6), $X^3$ and $X^4$ each independently represent a monovalent anionic monodentate ligand, PNP represents the tridentate ligand having the formula (2), (3) or (4), and CO represents carbon monoxide.

[8] A method for producing alcohols by hydrogenation of aldehydes or ketones, using the ruthenium complex of any one of [1] to [5] as a catalyst.

[9] A method for producing alcohols, aldehydes or hemiacetals by hydrogenation of esters, using the ruthenium complex of any one of [1] to [5] as a catalyst.

[10] A method for producing carbonyl compounds by dehydrogenation of alcohols, hemiacetals or hemiaminals, using the ruthenium complex of any one of [1] to [5] as a catalyst.

[11] A method for producing N-alkylamines by an N-alkylation via condensation of alcohols and amines, using the ruthenium complex of any one of [1] to [5] as a catalyst.

[12] The method for producing alcohols, aldehydes, hemiacetals, carbonyl compounds and an N-alkylamines of any one of [8] to [11], wherein a ruthenium complex having the following formula (5) and a primary alcohol and/or carbon monoxide are added, respectively to a reaction system to form a catalyst:

$$[RuX^1X^2(PNP)]_q \qquad (5)$$

wherein in the formula (5), $X^1$ and $X^2$ each independently represent a monovalent anionic monodentate ligand, PNP represents the tridentate ligand having the formula (2), (3) or (4), and q represents an integer of 1 or 2.

[13] A catalyst for an organic reaction, comprising the ruthenium complex of any one of [1] to [5].

[14] The catalyst for an organic reaction of [13], wherein the organic reaction is a reaction of reducing a functional group having an ester group using a hydrogen donor.

[15] The catalyst for an organic reaction of [13], wherein the organic reaction is a reaction of dehydrogenating alcohols, hemiacetals or hemiaminals to produce carbonyl compounds.

[16] The catalyst for an organic reaction of [13], wherein the organic reaction is an N-alkylation via condensation of alcohols and amines.

[17] The catalyst for an organic reaction of any one of [13] to [16], wherein the ruthenium complex is formed by adding a ruthenium complex having the following formula (5):

$$[RuX^1X^2(PNP)]_q \qquad (5)$$

wherein in the formula (5), $X^1$ and $X^2$ each independently represent a monovalent anionic monodentate ligand, PNP represents the tridentate ligand having the formula (2), (3) or (4), and q represents an integer of 1 or 2, and a primary alcohol and/or carbon monoxide to a reaction system.

Effects of the Invention

The ruthenium complex of the present invention can be easily prepared from a ruthenium compound, a tridentate ligand expressed as PNP and a primary alcohol (or carbon monoxide), is suitable for industrial use, and can perform a reaction at high catalytic activity under mild reaction conditions. For example, production of alcohols by hydrogenation of aldehydes, ketones and esters in the presence of a hydrogen donor; production of carbonyl compounds by dehydrogenation of alcohols; and production of N-alkylamines by an N-alkylation via condensation of alcohols and amines, can be performed.

BRIEF DESCRIPTION OF DRAWINGS

FIG. 1 shows an ORTEP drawing of X-ray structure analysis of a ruthenium complex B (Example 4).

DESCRIPTION OF EMBODIMENTS

The ruthenium complex having the formula (1) of the present invention is described below.

In formula (1), PNP represents a tridentate ligand having the formula (2):

In formula (2), $R^1$, $R^2$, $R^{1\prime}$ and $R^{2\prime}$ are described below.

Examples of the alkyl group include an alkyl group which may be linear, branched or cyclic. For example, an alkyl group having 1 to 50, preferably 1 to 20, and more preferably 1 to 10 carbon atom(s) is included. Specific examples thereof include a methyl group, an ethyl group, an n-propyl group, an isopropyl group, an n-butyl group, an isobutyl group, an s-butyl group, a tert-butyl group, an n-pentyl group, a 2-pentyl group, a 3-pentyl group, a tert-pentyl group, a 2-methylbutyl group, a 3-methylbutyl group, a 2,2-dimethylpropyl group, a 3-methylbutan-2-yl group, an n-hexyl group, an n-octyl group, a cyclopropyl group, a cyclopentyl group, a cyclohexyl group, a cyclooctyl group, a 1-bicyclo[2.2.1]heptyl group, a 2-bicyclo[2.2.1]heptyl group, a 1-bicyclo[2.2.2]octyl group, a 2-bicyclo[2.2.2]octyl group, a 1-adamantyl group (1-tricyclo[3.3.1.1]decyl group), a 2-adamantyl group (1-tricyclo[3.3.1.1]decyl group), and the like. An isopropyl group and a cyclohexyl group are preferred.

Examples of the aryl group include a monocyclic, polycyclic or fused cyclic aryl group having 6 to 36, preferably 6 to 18, and more preferably 6 to 14 carbon atoms. Specific examples thereof include a phenyl group, a 1-naphthyl group, a 2-naphthyl group, a 1-anthryl group, a 2-anthryl group, a 9-anthryl group, a 1-phenanthryl group, a 2-phenanthryl group, a 9-phenanthryl group, a 1-biphenyl group, a 2-biphenyl group, a 3-biphenyl group, and the like. A phenyl group is preferred.

Examples of the aralkyl group include a group in which at least one hydrogen atom of the above-described alkyl group is substituted with the above-described aryl group. Examples thereof include an aralkyl group having 7 to 37, preferably 7 to 20, and more preferably 7 to 15 carbon atoms. Specific examples thereof include a benzyl group, a 1-phenylethyl group, a 2-phenylethyl group, a 1-phenylpropyl group, and the like.

Examples of the alkenyl group include an alkenyl group which may be linear, branched or cyclic. For example, an alkenyl group having 2 to 20, preferably 2 to 15, and more preferably 2 to 10 carbon atoms is included. Specific examples thereof include a vinyl group, a 1-propenyl group, a 2-propenyl group, a 1-cyclohexenyl group, a 1-cycloheptenyl group, and the like.

Examples of the alkynyl group include an alkynyl group which may be linear or branched. For example, an alkynyl group having 2 to 20, preferably 2 to 15, and more preferably 2 to 10 carbon atoms is included. Specific examples thereof include an ethynyl group, a 1-propynyl group, a 2-propynyl group, and the like.

Examples of the alkoxy group include an alkoxy group which may be linear, branched or cyclic. For example, an alkoxy group containing an alkyl group having 1 to 20, preferably 1 to 15, and more preferably 1 to 10 carbon atom(s) is included. Specific examples thereof include a methoxy group, an ethoxy group, an n-propoxy group, an isopropoxy group, an n-butoxy group, an isobutoxy group, an s-butoxy group, a tert-butoxy group, an n-pentyloxy group, a cyclopropyloxy group, a cyclopentyloxy group, a cyclohexyloxy group, and the like.

Examples of the aryloxy group include an aryloxy group containing a monocyclic, polycyclic or fused cyclic aryl group having 6 to 36, preferably 6 to 18, and more preferably 6 to 14 carbon atoms. Specific examples thereof include a phenoxy group, a p-methylphenoxy group, a 1-naphthyloxy group, and the like.

Examples of the aralkyloxy group include a group in which at least one hydrogen atom of the alkyl group of the alkoxy group is substituted with the above-described aryl group, and for example, an aralkyloxy group having 7 to 20 and preferably 7 to 15 carbon atoms is included. Specific examples thereof include a benzyloxy group, a 1-phenylethoxy group, a 2-phenylethoxy group, a 1-phenylpropoxy group, a 2-phenylpropoxy group, a 3-phenylpropoxy group, a 4-phenylbutoxy group, a 1-naphthylmethoxy group, 2-naphthylmethoxy group, and the like.

Examples of the heterocyclic group include an aliphatic heterocyclic group and an aromatic heterocyclic group. Examples of the aliphatic heterocyclic group include 3 to 8-membered, preferably 4 to 6-membered monocyclic aliphatic heterocyclic group and polycyclic or fused cyclic aliphatic heterocyclic group having 2 to 14 carbon atoms and at least one, preferably 1 to 3 heteroatoms. Specific examples of the heteroatom include a nitrogen atom, an oxygen atom, and/or a sulfur atom, and the like. Specific examples of the aliphatic heterocyclic group include a 2-pyrrolidinyl group, a 2-piperidinyl group, a 2-piperazinyl group, a 2-morpholinyl group, a 2-tetrahydrofuryl group, a 2-tetrahydropyranyl group, 2-tetrahydrothienyl group, and the like.

Examples of the aromatic heterocyclic group include 5 or 6-membered monocyclic heteroaryl group and polycyclic or fused cyclic heteroaryl group having 2 to 15 carbon atoms and at least one, preferably 1 to 3 heteroatoms. Specific examples of the heteroatom include a nitrogen atom, an oxygen atom, and/or a sulfur atom, and the like. Specific examples of the aromatic heterocyclic group include a 2-furyl group, a 3-furyl group, a 2-thienyl group, a 3-thienyl group, a 2-pyridyl group, a 3-pyridyl group, a 2-pyrimidyl group, a 2-pyrazyl group, a 2-imidazolyl group, a 4-imidazolyl group, a 2-oxazolyl group, a 2-thiazolyl group, a 2-benzofuryl group, a 3-benzofuryl group, a 2-benzothienyl group, a 3-benzothienyl group, a 2-quinolyl group, a 3-quinolyl group, a 1-isoquinolyl group, a 2-benzoimidazolyl group, a 2-benzooxazolyl group, a 2-benzothiazolyl group, and the like.

The amino group may have substituent(s). For example, an amino group, and an amino group in which at least one hydrogen atom are independently substituted with the alkyl group, the aryl group, the aralkyl group, the alkenyl group or the alkynyl group described above is included. Specific examples thereof include an N,N-diethylamino group, an N,N-diisopropylamino group, an N,N-dicyclohexylamino group, an N,N-diphenylamino group, an N-naphthyl-N-phenylamino group, an N,N-dibenzylamino group, and the like. Further, when the amino group has two substituents, the substituents may bind to each other to form a ring. Specific examples thereof include a pyrrolidino group, a piperidino group, and the like. Further, examples of the amino group also include a piperazino group and a morpholino group.

These alkyl group, aryl group, aralkyl group, alkenyl group, alkynyl group, alkoxy group, aryloxy group, aralkyloxy group, and heterocyclic group may have substituent(s).

Examples of the substituents of the alkyl group, the aralkyl group, the alkenyl group, the alkynyl group, the alkoxy group, and the aralkyloxy group include a hydroxyl group, the above-described alkoxy group, the above-described aryloxy group, the above-described aralkyloxy group, the above-described heterocyclic group, the above-described amino group, a halogeno group, a silyl group, a siloxy group, an acyloxy group, and the like.

Examples of the substituents of the aryl group, the aryloxy group, and the heterocyclic group include the above-described alkyl group, the above-described aryl group, the above-described aralkyl group, the above-described alkenyl group, the above-described alkynyl group, the above-described heterocyclic group, a hydroxyl group, the above-described alkoxy group, the above-described aryloxy group, the above-described aralkyloxy group, the above-described amino group, a halogeno group, a halogenoalkyl group, a silyl group, a siloxy group, and an acyloxy group.

Examples of the halogeno group include a fluoro group, a chloro group, a bromo group, an iodo group, and the like.

Examples of the halogenoalkyl group include a group in which at least one hydrogen atom on the above-described alkyl group is substituted with a halogen atom. Specific examples thereof include a trifluoromethyl group, an n-nonafluorobutyl group, and the like. A trifluoromethyl group is preferred.

Examples of the silyl group include a group in which at least one hydrogen atom on the silyl group is substituted with the above-described alkyl group, the above-described aryl group, the above-described aralkyl group, and the like. Specific examples thereof include a trimethylsilyl group, a triethylsilyl group, a triisopropylsilyl group, a t-butyldimethylsilyl group, a t-butyldiphenylsilyl group, a triphenylsilyl group, and the like.

Examples of the siloxy group include a group in which the above-described silyl group is bonded to an oxygen atom. Specific examples thereof include a trimethylsiloxy group, a triethylsiloxy group, a triisopropylsiloxy group, a t-butyldimethylsiloxy group, a t-butyldiphenylsiloxy group, a triphenylsiloxy group, and the like.

Examples of the acyloxy group include an acyloxy group having 6 to 36, preferably 6 to 18, and more preferably 6 to 14 carbon atoms. Specific examples thereof include an acetyloxy group, a benzyloxycarbonyl group, and the like.

$R^1$ and $R^2$, and $R^{1'}$ and $R^{2'}$ independently may bind to each other to form a ring containing the adjacent phosphorus atom. Specific examples of the ring containing a phosphorus atom include phospholane, phosphor, phosphinan, 2,5-dioxaphospholane, 2,5-diazaphosphoridine, and the like. These groups may have substituent(s) as described above.

$Q^1$ and $Q^2$ in the formula (2) is described below.

$Q^1$ and $Q^2$ represent an optionally substituted alkanediyl group or an optionally substituted aralkylene group.

Examples of the alkanediyl group include an alkanediyl group which may be linear, branched or cyclic. For example, an alkanediyl group having 1 to 20, preferably 1 to 10, and more preferably 1 to 6 carbon atom(s) is included. Specific examples thereof include a methylene group, an ethylene group, a trimethylene group, a tetramethylene group, a pentamethylene group, a cyclopropan-1,2-diyl group, a cyclobutan-1,2-diyl group, a cyclobutan-1,3-diyl group, a cyclopentan-1,2-diyl group, a cyclopentan-1,3-diyl group, a cyclohexane-1,2-diyl group, a cyclohexane-1,3-diyl group, and the like. An ethylene group is preferred.

Examples of the aralkylene group include an aralkylenediyl group having 7 to 11 carbon atoms in which one hydrogen is removed from the aryl group on an aralkyl group such as a benzyl group and an a phenethyl group. Specific examples thereof include a benzylene group (-Ph-CH$_2$—), a 2-phenyl ethylene group (-Ph-CH$_2$CH$_2$—), a 1-naphthyl methylene group (—Np—CH$_2$—), a 2-naphthyl methylene group (—Np—CH$_2$—), and the like.

Examples of the substituents of these alkanediyl group and aralkylene group include a hydroxyl group, an alkoxy group, an aryloxy group, an aralkyloxy group, a heterocyclic group, an amino group, a halogeno group, a silyl group, a siloxy group, and an acyloxy group. Examples of these groups include the groups as described above.

Examples of preferred PNP include a tridentate ligand having the formula (3), and examples of more preferred PNP include a tridentate ligand having the formula (4).

In the formula (3), $R^7$, $R^{7'}$, $R^8$, $R^{8'}$, $R^9$, $R^{9'}$, $R^{10}$ and $R^{10'}$ are described below. Examples of the alkyl group, the aryl group, the aralkyl group, the alkenyl group, the alkynyl group, the alkoxy group, the aryloxy group, the aralkyloxy group, the heterocyclic group, and the amino group include the groups as described in detail in the description of $R^1$, $R^2$, $R^{1'}$, and $R^{2'}$ in the formula (2).

Further, these alkyl group, aryl group, aralkyl group, alkenyl group, alkynyl group, alkoxy group, aryloxy group, aralkyloxy group, and heterocyclic group may have substituent(s).

Examples of the substituents of the alkyl group, the aralkyl group, the alkenyl group, the alkynyl group, the alkoxy group, and the aralkyloxy group include a hydroxyl group, an alkoxy group, an aryloxy group, an aralkyloxy group, a heterocyclic group, an amino group, a halogeno group, a silyl group, a siloxy group, and an acyloxy group. Among these groups, examples of the alkoxy group, the aryloxy group, the aralkyloxy group, the heterocyclic group, the amino group, the halogeno group, the silyl group, the siloxy group, and the acyloxy group include the groups as described in detail in the description of $R^1$, $R^2$, $R^{1'}$, and $R^{2'}$ in the formula (2).

Examples of the aryl group, the aryloxy group, and the heterocyclic group include an alkyl group, an aryl group, an aralkyl group, an alkenyl group, an alkynyl group, a hydroxyl group, an alkoxy group, an aryloxy group, an aralkyloxy group, a heterocyclic group, an amino group, a halogeno group, a silyl group, a siloxy group, and an acyloxy group. Among these groups, examples of the alkyl group, the aryl group, the aralkyl group, the alkenyl group, the alkynyl group, the alkoxy group, the aryloxy group, the aralkyloxy group, the heterocyclic group, the amino group, the halogeno group, the silyl group, the siloxy group, and the acyloxy group include the groups as described in detail in the description of $R^1$, $R^2$, $R^{1'}$, and $R^{2'}$ in the formula (2).

In the formula (1), X and Y are described below.

In the formula (1), X represents a monovalent anionic monodentate ligand. The monovalent anionic monodentate ligand has a monovalent negative charge, and represents a functional group or an anion capable of being single-bonded to a metal in the metal complex. Specific examples thereof (a formula is shown in parentheses) include hydride (—H), a hydroxyl group (—OH), an alkoxy group (—OR), an aryloxy group (—OAr), an aralkyloxy group (—OAral), an acyloxy group (—OC(=O)R), a sulfonyloxy group (—OSO$_2$R), a halogeno group (—X), a hydrogen carbonate ion (HCO$_3^-$), a tetrahydroborate ion (BH$_4^-$), a tetrafluoroborate ion (BF$_4^-$), a tetraarylborate ion (BAr$_4^-$), a perchloric ion (ClO$_4^-$), a hexafluorophosphate ion (PF$_6^-$), a hexafluoroantimonate ion (SbF$_6^-$), a tetrahydroaluminate ion (AlH$_4^-$), a tetrahydroxoaluminate ion ([Al(OH)$_4$]$^-$), a bis(2-methoxyethoxy)dihydroaluminate ion (AlH$_2$(OCH$_2$CH$_2$OCH$_3$)$_2^-$), a trihydrocyanoborate ion (BH$_3$CN$^-$), a triethylhydroborate ion (BH(Et)$_3^-$), a tris(2-butyl)hydroborate ion (BH(sec-Bu)$_3^-$), and the like. Hydride (—H), a halogeno group (—X), and a tetrahydroborate ion (BH$_4^-$) are preferred, and hydride (—H) is more preferred.

Y in the formula (1) represents a counter anion. A counter anion represents an anion having a monovalent negative charge and capable of functioning as a counter ion in a metal complex. Specific examples thereof include a hydroxide ion (HO$^-$), an alkoxide ion (RO$^-$), an aryloxide ion (ArO$^-$), an aralkyloxide ion (AralO$^-$), a carboxylate ion (RCO$_2^-$), a sulfonate ion (RSO$_3^-$), a halide ion (X$^-$), a hydrogen carbonate ion (HCO$_3^-$), a tetrahydroborate ion (BH$_4^-$), a tetrafluoroborate ion (BF$_4^-$), a tetraarylborate ion (BAr$_4^-$), a perchlorate ion (ClO$_4^-$), a hexafluorophosphate ion (PF$_6^-$), a hexafluoroantimonate ion (SbF$_6^-$), a tetrahydroaluminate ion (AlH$_4^-$), a tetrahydroxoaluminate ion ([Al(OH)$_4$]$^-$), a bis(2-methoxyethoxy)dihydroaluminate ion (AlH$_2$(OCH$_2$CH$_2$OCH$_3$)$_2^-$), a trihydrocyanoborate ion (BH$_3$CN$^-$), a triethylhydroborate ion (BH(Et)$_3^-$), a tris(2-butyl)hydroborate ion (BH(sec-Bu)$_3^-$), and the like, and preferably a hydroxide ion (HO⁻), a halide ion (X⁻), a tetrafluoroborate ion (BF₄⁻), a tetraarylborate ion (BAr₄), a hexafluorophosphate ion (PF₆⁻), and the like. A halide ion (X⁻) and a tetraarylborate ion (BAr₄⁻) are preferred.

Examples of the alkoxy group/alkoxide ion include an alkoxy group/alkoxide ion having 1 to 10 carbon atoms, and preferably an alkoxy group/alkoxide ion having 1 to 4 carbon atoms. Specific examples thereof include a methoxy group/methoxide ion, an ethoxy group/ethoxide ion, a 1-propoxy group/1-propoxide ion, a 2-propoxy group/2-propoxide ion, a 1-butoxy group/1-butoxide ion, a 2-butoxy group/2-butoxide ion, a tert-butoxy group/tert-butoxide ion, and the like.

Examples of the aryloxy group/aryloxide ion include an aryloxy group/aryloxide ion having 6 to 14 carbon atoms, preferably an aryloxy group/aryloxide ion having 6 to 10 carbon atoms. Specific examples thereof include a phenoxy group/phenoxide ion, a p-methylphenoxy group/p-methylphenoxide ion, a 2,4,6-trimethylphenoxy group/2,4,6-trimethylphenoxide ion, a p-nitrophenoxy group/p-nitrophenoxide ion, a pentafluorophenoxy group/pentafluorophenoxide ion, a 1-naphthyloxy group/1-naphthyloxide ion, a 2-naphthyloxy group/2-naphthyloxide ion, and the like.

Examples of the aralkyloxy group/aralkyloxide ion include an aralkyloxy group/aralkyloxide ion having 7 to 20 carbon atoms, preferably an aralkyloxy group/aralkyloxide ion having 7 to 15 carbon atoms. Specific examples thereof include a benzyloxy group/benzyloxide ion, a 1-phenylethoxy group/1-phenylethoxide ion, a 2-phenylethoxy group/2-phenylethoxide ion, and the like.

Examples of the acyloxy group/carboxylate ion include a carboxyl group/carboxylate ion having 1 to 18, preferably 1 to 6 carbon atoms, and specific examples thereof include a formyloxy group/formate ion, an acetoxy group/acetate ion, a trifluoroacetoxy group/trifluoroacetate ion, a propanoyloxy group/propionate ion, an acryloyloxy group/acrylate ion, a butanoyloxy group/butyrate ion, a pivaloyloxy group/pivalate ion, a pentanoyloxy group/valerate ion, a hexanoyloxy group/caproate ion, a benzoyloxy group/benzoate ion, a pentafluorobenzoyloxy group/pentafluorobenzoate ion, and the like.

Specific examples of the sulfonyloxy group/sulfonate ion include a methanesulfonyloxy group/methanesulfonate ion, a trifluoromethanesulfonyloxy group/trifluoromethanesulfonate ion, an n-nonafluorobutanesulfonyloxy group/n-nonafluorobutanesulfonate ion, a p-toluenesulfonyloxy group/p-toluenesulfonate ion, a 10-camphorsulfonyloxy group/10-camphorsulfonate ion, and the like.

Specific examples of the halogeno group/halide ion include a fluoro group/fluoride ion, a chloro group/chloride ion, a bromo group/bromide ion, and an iodo group/iodide ion. A chloro group/chloride ion and an iodo group/iodide ion are preferred.

Specific examples of the tetraarylborate ion include a tetraphenylborate ion, a tetrakis(pentafluorophenyl)borate ion, a tetrakis[3,5-bis(trifluoromethyl)phenyl]borate ion, and the like.

The ruthenium complex of the present invention having the formula (1) can be easily produced from a ruthenium compound, PNP as a ligand, a primary alcohol and/or carbon monoxide.

The ruthenium compound is not particularly limited, but examples thereof include inorganic ruthenium compounds such as a ruthenium trichloride hydrate, a ruthenium tribromide hydrate, and a ruthenium triiodide hydrate, tetra(dimethylsulfoxide)dichlororuthenium (RuCl₂(DMSO)₄), a dichloro(1,5-cyclooctadiene)ruthenium(II) polymer ([Ru(cod)Cl₂]n), a dichloro(norbornadiene)ruthenium(II) polymer ([Ru(nbd)Cl₂]n), bis(2-metallyl) (1,5-cyclooctadiene) ruthenium(II) ((cod)Ru(2-methallyl)₂), a dichloro(benzene)ruthenium(II) dimer ([Ru(benzene)Cl₂]₂), a dibromo(benzene)ruthenium(II) dimer ([Ru(benzene)Br₂]₂), a diiodo(benzene)ruthenium(II) dimer ([Ru(benzene) I₂]₂), a dichloro(p-cymen)ruthenium(II) dimer ([Ru(p-cymene) Cl₂]₂), a dibromo(p-cymen) ruthenium(II) dimer ([Ru(p-cymene)Br₂]₂), a diiodo(p-cymen)ruthenium(II) dimer ([Ru(p-cymene) I₂]₂), a dichloro(mesitylene)ruthenium(II) dimer ([Ru(mesitylene)Cl₂]₂), a dibromo(mesitylene)ruthenium (II) dimer ([Ru(mesitylene)Br₂]₂), a diiodo(mesitylene)ruthenium(II) dimer ([Ru (mesitylene) I₂]₂), a dichloro(hexamethylbenzene)ruthenium(II) dimer ([Ru (hexamethylbenzene) Cl₂]₂), a dibromo(hexamethylbenzene)ruthenium(II) dimer ([Ru (hexamethylbenzene) Br₂]₂), a diiodo(hexamethylbenzene)ruthenium(II) dimer ([Ru (hexamethylbenzene) I₂]₂), dichlorotris(triphenyl)phosphine (RuCl₂ (PPh₃)₃), dibromotris(triphenyl)phosphine (RuBr₂ (PPh₃)₃), diiodotris(triphenyl)phosphine (RuI₂ (PPh₃)₃), tetrahydrotris(triphenylphosphine)ruthenium(IV) (RuH₄ (PPh₃)₃), hydrochlorotris(triphenylphosphine)ruthenium(II) (RuClH (PPh₃)₃), acetatotris(triphenylphosphine) ruthenium(II) (RuH(OAc) (PPh₃)₃), dihydrotetrakis(triphenylphosphine)ruthenium (II) (RuH₂(PPh₃)₄), and the like.

The primary alcohol is defined as an alcohol having a hydroxyl group bonded to a primary carbon, a polyhydric alcohol having hydroxyl groups bonded to primary carbon(s), and methanol. Specific examples thereof include methanol, ethanol, 1-propanol, 2-methyl-1-propanol, 1-butanol, 2-methyl-1-butanol, 3-methyl-1-butanol, 1-pentanol, ethylene glycol, propylene glycol, glycerol, 3-methoxy-1-butanol, and the like. Methanol is preferred.

Subsequently, a method for producing the ruthenium complex having the formula (1) of the present invention is described below. The ruthenium complex of the present invention can be obtained by reacting a ruthenium complex having the following formula (5):

$$[RuX^1X^2(PNP)]_q \qquad (5)$$

or a ruthenium complex having the following formula (6):

$$RuX^3X^4(CO)(PNP) \qquad (6)$$

with a primary alcohol and/or carbon monoxide.

In the formulae (5) and (6), X¹, X², X³, and X⁴ represent a monovalent anionic monodentate ligand which is the same as the monovalent anionic monodentate ligand described in detail in the formula (1), and may be the same as or different from X in the formula (1).

The produced ruthenium complex of the present invention may produce stereoisomers by coordination mode and conformation of the ligand. Specific examples thereof include the stereoisomers shown below.

[Chem. 4]

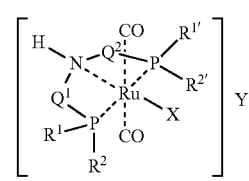

[A]

-continued

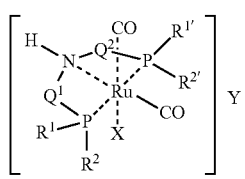 [B]

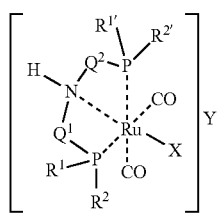 [C]

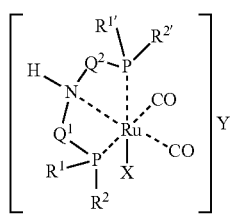 [D]

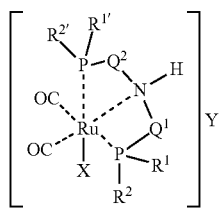 ent-[D]

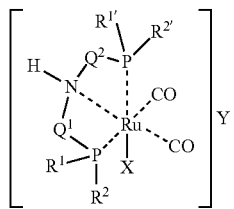 racemi-[D]

wherein $R^1$, $R^2$, $R^{1'}$, $R^{2'}$, $Q^1$, $Q^2$, X, and Y are as defined in the formula (1), a broken line between each symbol represents a coordinate bond, and a solid line between each symbol represents a covalent bond.

In the notation of the stereoisomers of each of the complexes, ent-[D] represents an enantiomer of [D], and racemi-[D] represents a racemic mixture of [D] and ent-[D]. The ruthenium complex of the present invention used in the reaction of the present invention may be a mixture of the stereoisomers or one pure isomer, but examples of a more preferred stereoisomer include [B]. Examples of a production method for obtaining pure [B] include a production method of reacting the ruthenium complex having the formula (5) or formula (6) with a primary alcohol and/or carbon monoxide.

In the production of the ruthenium complex having the formula (1), it is desirable to use a solvent. Specific examples of the solvent to be used include aliphatic hydrocarbons such as hexane and heptane, aromatic hydrocarbons such as toluene and xylene, halogenated hydrocarbons such as methylene chloride and chlorobenzene, ethers such as diethyl ether, tetrahydrofuran, methyl tert-butyl ether, and cyclopentyl methyl ether, alcohols such as methanol, ethanol, isopropylalcohol, n-butylalcohol, 2-butanol, and tert-butylalcohol, polyhydric alcohols such as ethylene glycol, propylene glycol, 1,2-propanediol, and glycerin, amides such as dimethylformamide and dimethylacetamide, nitriles such as acetonitrile, sulfoxides such as dimethylsulfoxide, water, and the like, and aliphatic hydrocarbons, aromatic hydrocarbons, ethers, alcohols, polyhydric alcohols, amides, nitriles, and sulfoxides are preferred. Specific examples thereof include tetrahydrofuran, methanol, ethanol, isopropylalcohol, dimethylformamide, acetonitrile, dimethylsulfoxide, and the like. Methanol is preferred. These solvents may be used alone or in appropriate combination of two or more.

It is desirable that the production method of the present invention is carried out under an inert gas, carbon monoxide gas or the air atmosphere. Specific examples of the inert gas include argon gas and nitrogen gas. These gases and the air atmosphere may be used alone or as a mixed gas. A reaction temperature is appropriately selected in a range of usually −50° C. to 300° C., preferably −20° C. to 250° C., and more preferably 30° C. to 200° C. A reaction time is naturally selected depending on a base, a solvent, a reaction temperature, and other condition, but is appropriately selected in a range of usually 1 minute to 72 hours, preferably 1 minute to 24 hours, and more preferably 5 minutes to 12 hours.

Further, an appropriate additive may be added to the production method of the present invention. Specific examples of the additive include a bronsted acid, a salt of a bronsted acid, a basic compound, and the like. Specific examples of the bronsted acid include hydrofluoric acid, hydrochloric acid, hydrobromic acid, hydroiodic acid, acetic acid, benzoic acid, trifluoromethane sulfonate, tetrafluoroboric acid, hexafluorophosphoric acid, and the like. Specific examples of the salt of a bronsted acid include a metal salt composed of a bronsted acid, and the like. More preferred specific examples thereof include metal halides, and the like. Still more preferred specific examples thereof include lithium chloride, lithium bromide, lithium iodide, sodium fluoride, sodium bromide, sodium iodide, potassium fluoride, potassium bromide, and the like. Specific examples of the basic compound include metal hydroxides such as lithium hydroxide, sodium hydroxide, potassium hydroxide, and cesium hydroxide, metal hydrides such as lithium hydride, sodium hydride, potassium hydride, lithium borohydride, sodium borohydride, potassium borohydride, aluminum lithium hydride, and diisobutyl aluminum hydride, metal alkoxides such as lithium methoxide, lithium isopropoxide, lithium tert-butoxide, sodium methoxide, sodium ethoxide, sodium isopropoxide, sodium tert-butoxide, potassium methoxide, potassium ethoxide, potassium isopropoxide, potassium tert-butoxide, and the like. Sodium borohydride, sodium methoxide, and potassium tert-butoxide are more preferred.

The ruthenium complex of the present invention produced by the production method of the present invention can be subjected to post-treatment, isolation, and purification, if necessary. Specific example of a method of post-treatment include concentration, solvent substitution, washing, extraction, back extraction, filtration, crystallization by addition of a poor solvent, and the like. These can be carried out alone or in combination. Specific examples of the method of isolation and purification include drying of a reaction solution, column chromatography, recrystallization, crystal washing with a poor solvent, and the like. These can be carried out alone or in combination.

The ruthenium complex having the formula (1) of the present invention is useful as a catalyst in hydrogenation of aldehydes, ketones, and esters. Further, the ruthenium complex having the formula (1) of the present invention is useful as a catalyst in dehydrogenation of alcohols, hemiacetals, and hemiaminals and an N-alkylation via condensation of alcohols and amines.

Accordingly, the present invention provides a ruthenium catalyst for an organic reaction, including the ruthenium complex having the formula (1).

A method for producing alcohols by hydrogenation of aldehydes or ketones is described below.

A method for producing alcohols by hydrogenation of aldehydes or ketones in the present invention is a method for producing alcohols from aldehydes or ketones using the ruthenium complex having the formula (1) and a hydrogen donor, and examples thereof include a method expressed as the following scheme (1):

[Chem. 5]

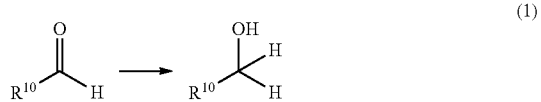

(1)

wherein $R^{10}$ represents an alkyl group, an aryl group, an aralkyl group, an alkenyl group, an alkynyl group, a heterocyclic group or a carbonyl group having one monovalent group, preferably an alkyl group or an aryl group, and further, these alkyl group, aryl group, aralkyl group, alkenyl group, alkynyl group, and heterocyclic group may have substituent(s), or a method expressed as the following scheme (2):

[Chem. 6]

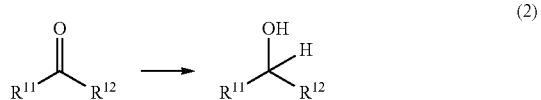

(2)

wherein $R^{11}$ and $R^{12}$, each independently represent an alkyl group, an aryl group, an aralkyl group, an alkenyl group, an alkynyl group, a heterocyclic group or a carbonyl group having one monovalent group, preferably an alkyl group or an aryl group, $R^{11}$ and $R^{12}$ may bind to each other to form a ring with the adjacent atom, and further, these alkyl group, aryl group, aralkyl group, alkenyl group, alkynyl group, and heterocyclic group may have substituent (s).

$R^{10}$, $R^{11}$, and $R^{12}$ in schemes (1) and scheme (2) are described below.

Examples of the alkyl group include an alkyl group which may be linear, branched or cyclic. For example, an alkyl group having 1 to 50, preferably 1 to 30, and more preferably 1 to 20 carbon atoms is included. Specific examples thereof include a methyl group, an ethyl group, an n-propyl group, an isopropyl group, an n-butyl group, an isobutyl group, an s-butyl group, a tert-butyl group, an n-pentyl group, a 2-pentyl group, a 3-pentyl group, a tert-pentyl group, a 2-methylbutyl group, a 3-methylbutyl group, a 2,2-dimethylpropyl group, a 3-methylbutan-2-yl group, an n-hexyl group, an n-octyl group, an n-nonyl group, an n-decyl group, n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosyl group, a cyclopropyl group, a cyclopentyl group, a cyclohexyl group, a cyclooctyl group, a 1-bicyclo[2.2.1]heptyl group, a 2-bicyclo[2.2.1]heptyl group, a 1-bicyclo[2.2.2]octyl group, a 2-bicyclo[2.2.2]octyl group, a 1-adamantyl group (1-tricyclo[3.3.1.1]decyl group), a 2-adamantyl group(1-tricyclo[3.3.1.1]decyl group), and the like. A methyl group, an ethyl group, an isopropyl group, a cyclohexyl group, and the like are preferred. A methyl group is still more preferred.

Examples of the aryl group include a monocyclic, polycyclic or fused cyclic aryl group having 6 to 36, preferably 6 to 18, and more preferably 6 to 14 carbon atoms. Specific examples thereof include a phenyl group, a 1-naphthyl group, a 2-naphthyl group, a 1-anthryl group, a 2-anthryl group, a 9-anthryl group, a 1-phenanthryl group, a 2-phenanthryl group, a 9-phenanthryl group, a 1-biphenyl group, a 2-biphenyl group, a 3-biphenyl group, and the like. A phenyl group is preferred.

Examples of the aralkyl group include a group in which at least one hydrogen atom of the above-described alkyl group is substituted with the above-described aryl group. Examples thereof include an aralkyl group having 7 to 50, preferably 7 to 30, and more preferably 7 to 20 carbon atoms. Specific examples thereof include a benzyl group, a 1-phenylethyl group, a 2-phenylethyl group, a 1-phenylpropyl group, a 1-phenylbutyl group, a 1-phenylpentyl group, a 1-phenylhexyl group, a 1-phenylheptyl group, a 1-phenyloctyl group, a 1-phenylnonyl group, a 1-phenyldecyl group, a 1-phenyl undecyl group, a 1-phenyl dodecyl group, a 1-phenyltridecyl group, 1-phenyltetradecyl group, and the like.

Examples of the alkenyl group include an alkenyl group which may be linear, branched or cyclic. For example, an alkenyl group having 2 to 50, preferably 2 to 30, and more preferably 2 to 20 carbon atoms is included. Specific examples thereof include a vinyl group, a 1-propenyl group, a 2-propenyl group, a 2-butenyl group, 2-pentenyl group, 2-hexenyl group, 2-heptenyl group, 2-octenyl group, 2-nonenyl group, 2-icosenyl group, 1-cyclohexenyl group, 1-cycloheptenyl group, and the like.

Examples of the alkynyl group include an alkynyl group which may be linear or branched, and for example, an alkynyl group having 2 to 50, preferably 2 to 30, and more preferably 2 to 20 carbon atoms is included. Specific examples thereof include an ethynyl group, a 1-propynyl group, a 2-propynyl group, a 2-butynyl group, 2-pentynyl group, 2-hexynyl group, 2-heptynyl group, 2-octynyl group, 2-nonynyl group, 2-icoxynyl group, and the like.

Examples of the heterocyclic group include an aliphatic heterocyclic group and an aromatic heterocyclic group. Examples of the aliphatic heterocyclic group include 3 to 8-membered, preferably 4 to 6-membered monocyclic aliphatic heterocyclic group and polycyclic or fused cyclic aliphatic heterocyclic group having 2 to 14 carbon atoms and at least one, preferably 1 to 3 heteroatoms. Specific examples of the heteroatom include a nitrogen atom, an oxygen atom, and/or a sulfur atom, and the like. Specific examples of the aliphatic heterocyclic group include a 2-pyrrolidinyl group, a 2-piperidinyl group, a 2-piperazinyl group, a 2-morpholinyl group, a 2-tetrahydrofuryl group, a 2-tetrahydropyranyl group, 2-tetrahydrothienyl group, and the like.

Examples of the aromatic heterocyclic group include 5 or 6-membered, monocyclic heteroaryl group, and polycyclic or fused cyclic heteroaryl group having 2 to 15 carbon atoms and at least one, preferably 1 to 3 heteroatoms. Specific examples of the heteroatom include a nitrogen atom, an oxygen atom, and/or a sulfur atom, and the like. Specific examples of the aromatic heterocyclic group include a 2-furyl group, a 3-furyl group, a 2-thienyl group, a 3-thienyl group, a 2-pyridyl group, a 3-pyridyl group, a 2-pyrimidyl group, a 2-pyrazyl group, a 2-imidazolyl group, a 4-imidazolyl group, a 2-oxazolyl group, a 2-thiazolyl group, a 2-benzofuryl group, a 3-benzofuryl group, a 2-benzothienyl group, a 3-benzothienyl group, a 2-quinolyl group, a 3-quinolyl group, a 1-isoquinolyl group, a 2-benzoimidazolyl group, a 2-benzooxazolyl group, a 2-benzothiazolyl group, and the like.

Examples of the carbonyl group having one monovalent group include a group having the following formula (A):

[Chem. 7]

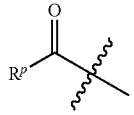

(A)

wherein $R^P$ represents a monovalent group, for example, a hydrogen atom, an alkyl group, an aryl group, an aralkyl group, an alkenyl group, an alkynyl group, a heterocyclic group, an alkoxy group, an aryloxy group, an aralkyloxy group, an amino group, a halogeno group or a halogenoalkyl group, and among the groups, an alkyl group, an aryl group, an aralkyl group, an alkenyl group, an alkynyl group, a heterocyclic group, an alkoxy group, an aryloxy group, an aralkyloxy group, and a halogenoalkyl group may have substituent(s).

$R^P$ in the formula (A) is described below. Examples of the alkyl group, the aryl group, the aralkyl group, the alkenyl group, the alkynyl group, and the heterocyclic group include the groups as described above.

Examples of the alkoxy group include an alkoxy group which may be linear, branched or cyclic. For example, an alkoxy group having 1 to 50, preferably 1 to 30, and more preferably 1 to 20 carbon atoms is included. Specific examples thereof include a methoxy group, an ethoxy group, an n-propoxy group, an isopropoxy group, an n-butoxy group, an isobutoxy group, an s-butoxy group, a tert-butoxy group, an n-pentyloxy group, an n-hexyloxy group, an n-heptyloxy group, an n-octyloxy group, an n-nonyloxy group, an n-decyloxy group, an n-undecyloxy group, an n-dodecyloxy group, an n-tridecyloxy group, an n-tetradecyloxy group, an n-pentadecyloxy group, an n-hexadecyloxy group, an n-heptadecyloxy group, an n-octadecyloxy group, an n-nonadecyloxy group, an n-icosyloxy group, a cyclopropyloxy group, a cyclopentyloxy group, a cyclohexyloxy group, and the like.

Examples of the aryloxy group include aryloxy groups containing a monocyclic, polycyclic or fused cyclic aryl group having 6 to 36, preferably 6 to 18, and more preferably 6 to 14 carbon atoms. Specific examples thereof include a phenoxy group, a p-methylphenoxy group, a 1-naphthyloxy group, and the like.

Examples of the aralkyloxy group include a group in which at least one hydrogen atom of the alkyl group of the above-described alkoxy group is substituted with the above-described aryl group. For example, an aralkyloxy group having 7 to 15 carbon atoms is included. Specific examples thereof include a benzyloxy group, a 1-phenylethoxy group, a 2-phenylethoxy group, a 1-phenylpropoxy group, a 2-phenylpropoxy group, a 3-phenylpropoxy group, a 4-phenylbutoxy group, a 1-naphthylmethoxy group, 2-naphthylmethoxy group, and the like.

The amino group may have substituent(s). For example, an amino group in which at least one hydrogen atom of the amino group is independently substituted with the alkyl group, the aryl group, the alkenyl group, the alkynyl group or the aralkyl group described above is included. Specific examples thereof include an N,N-diethylamino group, an N,N-diisopropylamino group, an N,N-dibutylamino group, an N,N-dipentylamino group, an N,N-didecylamino group, an N,N-dicyclohexylamino group, an N,N-diphenylamino group, an N-naphthyl-N-phenylamino group, an N,N-dibenzylamino group, and the like. Further, when the amino group has two substituents, the substituents may bind to each other to form a ring. Specific examples thereof include a pyrrolidino group, a piperidino group, and the like. Further, examples of the amino group also include a piperazino group and a morpholino group.

Examples of the halogeno group include a fluoro group, a chloro group, a bromo group, an iodo group, and the like.

Examples of the halogenoalkyl group include a group in which at least one hydrogen atom on the above-described alkyl group is substituted with a halogen atom. Specific examples thereof include a trifluoromethyl group, an n-nonafluorobutyl group, and the like. A trifluoromethyl group is preferred.

When $R^P$ is these alkyl group, aryl group, aralkyl group, alkenyl group, alkynyl group, heterocyclic group, alkoxy group, aryloxy group, aralkyloxy group or halogenoalkyl group, $R^P$ may have substituent(s). Examples of the substituent which $R^P$ may have when $R^P$ is an alkyl group, an aralkyl group, an alkenyl group, an alkynyl group or a halogenoalkyl group include a heterocyclic group, a hydroxyl group, an oxo group, an alkoxy group, an aryloxy group, an aralkyloxy group, an amino group, a halogeno group, a silyl group, a siloxy group, and an acyloxy group. Among these groups, examples of the heterocyclic group, the alkoxy group, the aryloxy group, the aralkyloxy group, the amino group, and the halogeno group include the groups as described above.

Examples of the silyl group include a group in which at least one hydrogen atom on the silyl group is substituted with the alkyl group, the aryl group, the aralkyl group described above, and the like. Specific examples thereof include a trimethylsilyl group, a triethylsilyl group, a triisopropylsilyl group, a t-butyldimethylsilyl group, a t-butyldiphenylsilyl group, a triphenylsilyl group, and the like.

Examples of the siloxy group include a group in which the above-described silyl group is bonded to an oxygen atom. Specific examples thereof include a trimethylsiloxy group, a triethylsiloxy group, a triisopropylsiloxy group, a t-butyldimethylsiloxy group, a t-butyldiphenylsiloxy group, a triphenylsiloxy group, and the like.

Examples of the acyloxy group include an acyloxy group which may be linear, branched or cyclic. For example, an acyloxy group having 1 to 50, preferably 2 to 30, and more preferably 1 to 20 carbon atoms is included. Specific examples thereof include an acetoxy group, a benzoyloxy group, a pivaloyloxy group (2,2-dimethylpropanoyloxy group), an n-butanoyloxy group, an n-pentanoyloxy group, an n-hexanoyloxy group, n-heptanoyloxy group, an n-octanoyloxy group, an n-nonanoyloxy group, an n-decanoyloxy group, an n-undecanoyloxy group, an n-dodecanoyloxy group, and the like.

Examples of the substituent which $R^P$ may have when $R^P$ is an aryl group, a heterocyclic group, an alkoxy group, an aryloxy group or an aralkyloxy group include an alkyl group, an aryl group, an aralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, and an acyloxy group. Among these groups, examples of the alkyl group, the aryl group, the aralkyl group, the alkenyl group, the alkynyl group, the heterocyclic group, the alkoxy group, the aryloxy group, the aralkyloxy group, the amino group, the halogeno group, the halogenoalkyl group, the silyl group, the siloxy group, and the acyloxy group include the groups as described above.

In scheme (1) and scheme (2), these alkyl group, aryl group, aralkyl group, alkenyl group, alkynyl group, and heterocyclic group may have substituent(s).

Examples of the substituents of the alkyl group, the aralkyl group, the alkenyl group, and the alkynyl group include a heterocyclic group, a hydroxyl group, an alkoxy group, an aryloxy group, an aralkyloxy group, an amino group, a halogeno group, a silyl group, a siloxy group, an acyloxy group, and a carbonyl group. Among these groups, examples of the heterocyclic group, the alkoxy group, the aryloxy group, the aralkyloxy group, the amino group, the halogeno group, the silyl group, the siloxy group, the acyloxy group, and the carbonyl group include the groups as described above.

Examples of the substituent of the aryl group and the heterocyclic group include an alkyl group, an aryl group, an aralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group, and a carbonyl group. Among these groups, examples of the alkyl group, the aryl group, the aralkyl group, the alkenyl group, the alkynyl group, the heterocyclic group, the alkoxy group, the aryloxy group, the aralkyloxy group, the amino group, the halogeno group, the halogenoalkyl group, the silyl group, the siloxy group, the acyloxy group, and the carbonyl group include the groups as described above.

In scheme (2), when $R^{11}$ and $R^{12}$ bind to each other to form a ring with the adjacent atom, ketones should be cyclic ketones.

In scheme (1) and scheme (2), when $R^{10}$, $R^{11}$, and $R^{12}$ are, independently of each other, a carbonyl group, an alkenyl group or an alkynyl group having one monovalent group, or $R^{10}$, $R^{11}$, and $R^{12}$, independently of each other, have a carbonyl group, an alkenyl group, an alkynyl group, and/or an acyloxy group having one monovalent group as a substituent, these groups may be reduced in the course of the reaction.

When $R^{10}$, $R^{11}$, and $R^{12}$, independently of each other, have an aralkyloxy group as a substituent, the aralkyloxy group may be reduced in the course of the reaction.

When PNP having the formula (2) is an optically active substance, an alcohol in which one enantiomer is in excess may be obtained as a product in scheme (2).

The hydrogenation reaction from aldehydes or ketones to alcohols in the present invention can be suitably carried out in the absence or presence of a solvent, but it is desirable to use a solvent. Examples of the preferred solvents include aromatic hydrocarbons such as toluene and xylene, aliphatic hydrocarbons such as hexane and heptane, halogenated hydrocarbons such as methylene chloride and chlorobenzene, ethers such as diethyl ether, tetrahydrofuran, methyl tert-butyl ether, and cyclopentyl methyl ether, alcohols such as methanol, ethanol, isopropylalcohol, n-butylalcohol, 2-butanol, and tert-butylalcohol, polyhydric alcohols such as ethylene glycol, propylene glycol, 1,2-propanediol, and glycerin, water, and the like. Toluene, tetrahydrofuran, and methanol are more preferred. These solvents may be used alone or in appropriate combination of two or more.

Examples of the hydrogen donor used in the method of the present invention include hydrogen gas, formic acid, a primary alcohol, and a secondary alcohol. Specific examples thereof include hydrogen gas, methanol, ethanol, 1-butanol, isopropanol, and the like. Hydrogen gas is more preferred.

A use amount of the catalyst varies depending on a substrate, reaction conditions, the type of catalyst, and the like, but is usually in a range of 0.0001 mol % to 20 mol % (a substance amount of the ruthenium complex per a substance amount of a substrate), preferably 0.002 mol % to 10 mol %, and more preferably 0.005 mol % to 5 mol %.

In the hydrogenation of aldehydes or ketones of the present invention, an appropriate additive may be added. Examples of the additive include a salt of a bronsted acid, a basic compound, and the like. Specific examples of the salt of a bronsted acid include a metal salt composed of a bronsted acid, and the like. More specific examples thereof include metal halides, and the like. Still more preferred examples thereof include lithium chloride, lithium bromide, lithium iodide, sodium fluoride, sodium bromide, sodium iodide, potassium fluoride, potassium bromide, and the like. Specific examples of the basic compound include amines such as triethylamine, diisopropylethylamine, N,N-dimethylaniline, piperidine, pyridine, 4-dimethylaminopyridine, 1,5-diazabicyclo[4.3.0]nona-5-en, 1,8-diazabicyclo[5.4.0]undeca-7-en, tri-n-butylamine, and N-methylmorpholine, alkali metal carbonates such as potassium carbonate, sodium carbonate, lithium carbonate, and cesium carbonate, alkaline earth metal carbonates such as magnesium carbonate and potassium carbonate, alkali metal hydrogen carbonates such as sodium hydrogen carbonate and potassium hydrogen carbonate, alkali metal hydroxides such as sodium hydroxide, potassium hydroxide, and lithium hydroxide, alkaline earth metal hydroxides such as magnesium hydroxide and potassium hydroxide, alkali metal alkoxides such as sodium methoxide, sodium ethoxide, sodium isopropoxide, sodium tert-butoxide, potassium methoxide, potassium ethoxide, potassium isopropoxide, potassium tert-butoxide, lithium methoxide, lithium isopropoxide, and lithium tert-butoxide, alkaline earth metal alkoxides such as magnesium methoxide and magnesium ethoxide, and metal hydrides such as sodium hydride, potassium hydride, lithium borohydride, sodium borohydride, potassium borohydride, and lithium aluminum hydride. Sodium methoxide, potassium tert-butoxide, sodium borohydride, and the like are preferred. A use amount of these additives is not particularly limited as long as the reaction proceeds, but it is possible to obtain a sufficiently high conversion rate even by using 10 mol % or less of the substrate.

The pressure at which hydrogenation is carried out using hydrogen gas as a hydrogen donor is usually under atmospheric pressure to 20 MPa, preferably under atmospheric pressure to 10 MPa, and more preferably under atmospheric pressure to 5 MPa. In addition, atmospheric pressure means a pressure under atmospheric pressure of hydrogen gas which does not require additional pressure of hydrogen gas.

A reaction temperature is appropriately selected in a range of usually −50° C. to 250° C., preferably −20° C. to 200° C., and more preferably 0° C. to 150° C.

A reaction time is naturally selected depending on a solvent, a reaction temperature, and other condition, but is appropriately selected in a range of usually 1 minute to 72 hours, preferably 1 minute to 24 hours, and more preferably 5 minutes to 12 hours.

The product can be subjected to post treatment, isolation, and purification, if necessary. Specific examples of a method of post-treatment include concentration, washing, extraction, back extraction, crystallization by addition of a poor solvent, and the like. These can be carried out alone or in combination. Specific examples of a method of isolation and purification include drying of a reaction solution, various chromatography, distillation, recrystallization, crystal washing with a poor solvent, and the like, and these can be carried out alone or in combination.

Subsequently, a method for producing alcohols, aldehydes, and hemiacetals by hydrogenation of esters is described.

In the present invention, examples of the method for producing alcohols, aldehydes, and hemiacetals by hydrogenation of esters include a method expressed as the following scheme (3):

[Chem. 8]

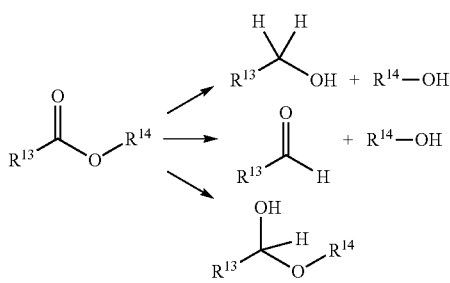

(3)

wherein $R^{13}$ represents a hydrogen atom, an alkyl group, an aryl group, an aralkyl group, an alkenyl group, an alkynyl group, a heterocyclic group or a carbonyl group having one monovalent group, and preferably represents an alkyl group, an aryl group or a heterocyclic group, and further, among these groups, an alkyl group, an aryl group, an aralkyl group, an alkenyl group, an alkynyl group, and a heterocyclic group may have substituent(s), $R^{14}$ represents an alkyl group, an aryl group, an aralkyl group, an alkenyl group, an alkynyl group or a heterocyclic group, preferably an alkyl group, and further, these alkyl group, aryl group, aralkyl group, alkenyl group, alkynyl group, and heterocyclic group may have substituent(s), and further, $R^{13}$ and $R^{14}$ may bind to each other.

$R^{13}$ and $R^{14}$ in scheme (3) are described below.

Examples of the alkyl group, the aryl group, the aralkyl group, the alkenyl group, the alkynyl group, the heterocyclic group, and a carbonyl group having one monovalent group of $R^{13}$ in scheme (3) include the groups as described in detail in the description for $R^{10}$, $R^{11}$, and $R^{12}$ in schemes (1) and (2).

Further, among these groups, the alkyl group, the aryl group, the aralkyl group, the alkenyl group, the alkynyl group, and the heterocyclic group may have substituent(s).

Examples of the substituents which the alkyl group, the aralkyl group, the alkenyl group or the alkynyl group may have include a heterocyclic group, a hydroxyl group, an alkoxy group, an aryloxy group, an aralkyloxy group, an amino group, a halogeno group, a silyl group, a siloxy group, an acyloxy group, and a carbonyl group having one monovalent group. Among these groups, examples of the heterocyclic group, the alkoxy group, the aryloxy group, the aralkyloxy group, the amino group, the halogeno group, the silyl group, the siloxy group, the acyloxy group, and the carbonyl group having one monovalent group include the groups as described in detail in the description for $R^{10}$, $R^{11}$, and $R^{12}$ in schemes (1) and (2).

Examples of the substituent which the aryl group or the heterocyclic group may have include an alkyl group, an aryl group, an aralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group, and a carbonyl group having one monovalent group. Among these groups, examples of the alkyl group, the aryl group, the aralkyl group, the alkenyl group, the alkynyl group, the heterocyclic group, the alkoxy group, the aryloxy group, the aralkyloxy group, the amino group, the halogeno group, the halogenoalkyl group, the silyl group, the siloxy group, the acyloxy group, and the carbonyl group having one monovalent group include the groups as described in detail in the description for $R^{10}$, $R^{11}$, and $R^{12}$ in schemes (1) and (2).

Examples of the alkyl group, the aryl group, the aralkyl group, the alkenyl group, the alkynyl group, and the heterocyclic group of $R^{14}$ in Scheme (3) include the groups as described in detail in the description for $R^{10}$, $R^{11}$, and $R^{12}$ in schemes (1) and (2).

Further, these groups may have substituent(s).

Examples of the substituents which the alkyl group, the aralkyl group, the alkenyl group or the alkynyl group may have include a heterocyclic group, a hydroxyl group, an alkoxy group, an aryloxy group, an aralkyloxy group, an amino group, a halogeno group, a silyl group, a siloxy group, an acyloxy group, and a carbonyl group having one monovalent group. Among these groups, examples of the heterocyclic group, the alkoxy group, the aryloxy group, the aralkyloxy group, the amino group, the halogeno group, the silyl group, the siloxy group, the acyloxy group, and the carbonyl group having one monovalent group include the groups as described in detail in the description for $R^{10}$, $R^{11}$, and $R^{12}$ in schemes (1) and (2).

Examples of the substituent which the aryl group or the heterocyclic group may have an alkyl group, an aryl group, an aralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group, and a carbonyl group having one monovalent group. Among these groups, examples of the alkyl group, the aryl group, the aralkyl group, the alkenyl group, the alkynyl group, the heterocyclic group, the alkoxy group, the aryloxy group, the aralkyloxy group, the amino group, the halogeno group, the halogenoalkyl group, the silyl group, the siloxy group, the acyloxy group, and the carbonyl group having one monovalent group include the groups as described in detail in the description for $R^{10}$, $R^{11}$, and $R^{12}$ in schemes (1) and (2).

When $R^{13}$ and $R^{14}$ bind to each other, esters should be cyclic compounds such as lactones.

When $R^{13}$ is a carbonyl group having one monovalent group, or when $R^{13}$ and $R^{14}$, independently of each other, have a carbonyl group having one monovalent group as a substituent, the carbonyl group having one monovalent group may be reduced in the course of the reaction.

When $R^{13}$ and $R^{14}$, independently of each other, represent an alkenyl group or an alkynyl group, or when $R^{13}$ and $R^{14}$, independently of each other, have an alkenyl group, an alkynyl group, and/or an acyloxy group as a substituent, these groups may be reduced in the course of the reaction.

When $R^{13}$ and $R^{14}$, independently of each other, have an aralkyloxy group as a substituent, the aralkyloxy group may be reduced in the course of the reaction.

The hydrogenation of esters of the present invention can be suitably carried out in the absence or presence of a solvent, but it is desirable to use a solvent. Examples of the solvent include the solvents as described in detail in the hydrogenation of aldehydes or ketones.

Examples of the hydrogen donor used in the hydrogenation of esters of the present invention include a hydrogen donor similar to the hydrogen donors as described in detail in the hydrogenation of aldehydes or ketones.

A use amount of the catalyst varies depending on a substrate, reaction conditions, the type of catalyst, and the like, but is usually in a range of 0.0001 mol % to 20 mol % (a substance amount of the ruthenium complex per a substance amount of a substrate), preferably 0.002 mol % to 10 mol %, and more preferably 0.005 mol % to 5 mol %.

Further, in the hydrogenation of esters of the present invention, an appropriate additive may be added. Examples of the additive include the additives as described in detail in the hydrogenation of aldehydes or ketones.

The pressure at which hydrogenation is carried out using hydrogen gas as a hydrogen donor is usually under atmospheric pressure to 20 MPa, preferably under atmospheric pressure to 10 MPa, and more preferably under atmospheric pressure to 5 MPa. In addition, atmospheric pressure means a pressure under atmospheric pressure of hydrogen gas which does not require additional pressure of hydrogen gas.

A reaction temperature is appropriately selected in a range of usually −50° C. to 250° C., preferably −20° C. to 200° C., and more preferably 0° C. to 150° C.

A reaction time is naturally selected depending on a solvent, a reaction temperature, and other condition, but is appropriately selected in a range of usually 1 minute to 72 hours, preferably 1 minute to 24 hours, and more preferably 5 minutes to 12 hours.

The product can be subjected to post treatment, isolation, and purification, if necessary. Specific examples of a method of post-treatment include concentration, washing, extraction, back extraction, crystallization by addition of a poor solvent, and the like. These can be carried out alone or in combination. Specific examples of isolation and purification methods include drying of a reaction solution, various chromatography, distillation, recrystallization, crystal washing with a poor solvent, and the like, and these can be carried out alone or in combination.

Subsequently, a method for producing carbonyl compounds which oxidizes alcohols, hemiacetals, and hemiaminals is described.

A method for producing carbonyl compounds by dehydrogenation of alcohols, hemiacetals, and hemiaminals in the present invention is for example, expressed as the following schemes (4), (5), and (6):

[Chem. 9]

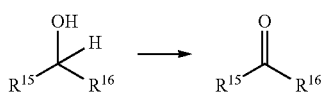
(4)

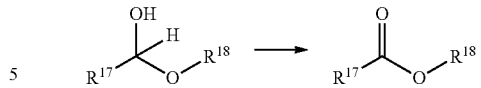
(5)

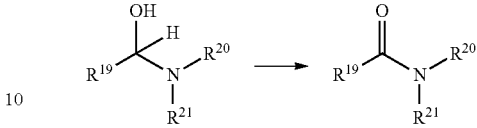
(6)

wherein $R^{15}$, $R^{16}$, $R^{17}$, and $R^{19}$, independently of one another, represent a hydrogen atom, an alkyl group, an aryl group, an aralkyl group, an alkenyl group, an alkynyl group, a heterocyclic group, an alkoxy group, an aryloxy group, an aralkyloxy group or a carbonyl group having one monovalent group, preferably, represent an alkyl group, an aryl group, an aralkyl group, an alkenyl group, an alkynyl group or a heterocyclic group, and more preferably, represent an alkyl group or an aryl group, and further, these alkyl group, aryl group, aralkyl group, alkenyl group, alkynyl group, heterocyclic group, alkoxy group, aryloxy group, and aralkyloxy group may have substituent(s), $R^{18}$ represents an alkyl group, an aryl group, an aralkyl group, an alkenyl group, an alkynyl group or a heterocyclic group, and these alkyl group, aryl group, aralkyl group, alkenyl group, alkynyl group and heterocyclic group may have substituent(s), $R^{20}$ and $R^{21}$, independently of each other, represent a hydrogen atom, an alkyl group, an aryl group, an aralkyl group, an alkenyl group, an alkynyl group or a heterocyclic group, and these alkyl group, aryl group, aralkyl group, alkenyl group, alkynyl group, and heterocyclic group may have substituent (s), and further, $R^{15}$ and $R^{16}$ in scheme (4) may bind to each other, $R^{17}$ and $R^{18}$ in scheme (5) may bind to each other, and $R^{19}$ and $R^{20}$ and/or $R^{21}$, or $R^{21}$ and $R^{20}$ in scheme (6) may bind to each other.

$R^{15}$, $R^{16}$, $R^{17}$, $R^{18}$, $R^{19}$, $R^{20}$, and $R^{21}$ in schemes (4), (5), and (6) are described below.

Examples of the alkyl group, the aryl group, the aralkyl group, the alkenyl group, the alkynyl group, the heterocyclic group, the alkoxy group, the aryloxy group, the aralkyloxy group, and a carbonyl group having one monovalent group in $R^{15}$, $R^{16}$, $R^{17}$, and $R^{19}$ in schemes (4), (5), and (6) include the groups as described in detail in the description for $R^{10}$, $R^{11}$, and $R^{12}$ in schemes (1) and (2).

Further, among these groups, the alkyl group, the aryl group, the aralkyl group, the alkenyl group, the alkynyl group, the heterocyclic group, the alkoxy group, the aryloxy group, and the aralkyloxy group may have substituent(s).

Examples of the substituents which the alkyl group, the aralkyl group, the alkenyl group or the alkynyl group may have include a heterocyclic group, a hydroxyl group, an alkoxy group, an aryloxy group, an aralkyloxy group, an amino group, a halogeno group, a silyl group, a siloxy group, an acyloxy group, and a carbonyl group having one monovalent group. Among these groups, examples of the heterocyclic group, the alkoxy group, the aryloxy group, the aralkyloxy group, the amino group, the halogeno group, the silyl group, the siloxy group, the acyloxy group, and the carbonyl group having one monovalent group include the groups as described in detail in the description for $R^{10}$, $R^{11}$, and $R^{12}$ in schemes (1) and (2).

Examples of the substituent which the aryl group, the heterocyclic group, the alkoxy group, the aryloxy group or the aralkyloxy group may have include an alkyl group, an aryl group, an aralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group, and a carbonyl group having one monovalent group. Among these groups, examples of the alkyl group, the aryl group, the aralkyl group, the alkenyl group, the alkynyl group, the heterocyclic group, the alkoxy group, the aryloxy group, the aralkyloxy group, the amino group, the halogeno group, the halogenoalkyl group, the silyl group, the siloxy group, the acyloxy group, and the carbonyl group having one monovalent group include the groups as described in detail in the description for $R^{10}$, $R^{11}$, and $R^{12}$ in schemes (1) and (2).

$R^{18}$ in scheme (5) is described below.

Examples of the alkyl group, the aryl group, the aralkyl group, the alkenyl group, the alkynyl group, and the heterocyclic group include the groups as described in detail in the description for $R^{10}$, $R^{11}$, and $R^{12}$ in schemes (1) and (2). Further, these groups may have substituent(s).

Examples of the substituents which the alkyl group, the aralkyl group, the alkenyl group or the alkynyl group may have include a heterocyclic group, a hydroxyl group, an alkoxy group, an aryloxy group, an aralkyloxy group, an amino group, a halogeno group, a silyl group, a siloxy group, an acyloxy group, and a carbonyl group having one monovalent group. Among these groups, examples of the heterocyclic group, the alkoxy group, the aryloxy group, the aralkyloxy group, the amino group, the halogeno group, the silyl group, the siloxy group, the acyloxy group, and the carbonyl group having one monovalent group include the groups as described in detail in the description for $R^{10}$, $R^{11}$, and $R^{12}$ in schemes (1) and (2).

Examples of the substituent which the aryl group or the heterocyclic group may have an alkyl group, an aryl group, an aralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group, and a carbonyl group having one monovalent group. Among these groups, examples of the alkyl group, the aryl group, the aralkyl group, the alkenyl group, the alkynyl group, the heterocyclic group, the alkoxy group, the aryloxy group, the aralkyloxy group, the amino group, the halogeno group, the halogenoalkyl group, the silyl group, the siloxy group, the acyloxy group, and the carbonyl group having one monovalent group include the groups as described in detail in the description for $R^{10}$, $R^{11}$, and $R^{12}$ in schemes (1) and (2).

When $R^{15}$ and $R^{16}$ in scheme (4) bind to each other, alcohols should be cyclic compounds such as cyclic alcohols. When $R^{17}$ and $R^{18}$ in scheme (5) bind to each other, hemiacetals should be cyclic compounds. When $R^{19}$ and $R^{20}$ and/or $R^{21}$ in scheme (6) bind to each other, hemiaminals should be cyclic compounds.

Further, when $R^{20}$ and $R^{21}$ bind to each other, hemiaminals should be cyclic compounds.

In schemes (4) to scheme (6), when $R^{15}$ to $R^{21}$, independently of each other, have a hydroxyl group as a substituent, the hydroxyl group may be oxidized in the course of the reaction.

Further, the hemiacetals in scheme (5) may be formed in the reaction system, and examples thereof include a method expressed as the following scheme (7):

[Chem. 10]

$$R^{17}CH(H)OH + R^{18}-OH \longrightarrow \left(R^{17}\underset{O-R^{18}}{\overset{OH}{\underset{|}{C}}}H\right) \longrightarrow R^{17}C(=O)O-R^{18} \quad (7)$$

$$R^{17}C(=O)H + R^{18}-OH$$

wherein $R^{17}$ and $R^{18}$ represent the groups as defined in scheme (5).

The hemiaminals in scheme (6) may be formed in the reaction system, and examples thereof include a method expressed as the following scheme (8):

[Chem. 11]

$$R^{19}CH(H)OH + R^{20}-NH-R^{21} \longrightarrow \left(R^{19}\underset{N(R^{21})-R^{20}}{\overset{OH}{\underset{|}{C}}}H\right) \longrightarrow R^{19}C(=O)N(R^{21})-R^{20} \quad (8)$$

$$R^{19}C(=O)H + R^{20}-NH-R^{21}$$

wherein $R^{19}$, $R^{20}$, and $R^{21}$ represent the groups as defined in scheme (6).

The dehydrogenation of alcohols, hemiacetals, and hemiaminals of the present invention can be suitably carried out in the absence or presence of a solvent, but it is desirable to use a solvent. Examples of the preferred solvents include aromatic hydrocarbons such as toluene and xylene, aliphatic hydrocarbons such as hexane and heptane, halogenated hydrocarbons such as methylene chloride and chlorobenzene, ethers such as diethylether, tetrahydrofuran, methyl-tert-butylether, and cyclopentylmethylether, and ketones such as 1-phenylethanone and benzophenone. Toluene and xylene are more preferred.

A use amount of the catalyst varies depending on a substrate, reaction conditions, the type of catalyst, and the like, but is usually in a range of 0.0001 mol % to 20 mol % (a substance amount of the ruthenium complex per a substance amount of a substrate), preferably 0.002 mol % to 10 mol %, and more preferably 0.005 mol % to 5 mol %.

Further, in the dehydrogenation of alcohols, hemiacetals, and hemiaminals of the present invention, an appropriate additive may be added. Examples of the additive include the additives as described in detail in the hydrogenation of ketones and aldehydes.

It is desirable that the present reaction is carried out under an inert gas or the air atmosphere. Specific examples of the inert gas include argon gas and nitrogen gas. These inert gases and air atmosphere may be used alone or as a mixed gas.

A reaction temperature is appropriately selected in a range of usually −50° C. to 300° C., preferably 0° C. to 200° C., and more preferably 20° C. to 150° C.

A reaction time is naturally selected depending on a solvent, a reaction temperature, and other conditions, but is appropriately selected in a range of usually 1 minute to 72 hours, preferably 1 minute to 24 hours, and more preferably 5 minutes to 12 hours.

The product can be subjected to post treatment, isolation, and purification, if necessary. Specific examples of a method of post-treatment include concentration, washing, extraction, back extraction, crystallization by addition of a poor solvent, and the like. These can be carried out alone or in combination. Specific examples of the method of isolation and purification include drying of a reaction solution, various chromatography, distillation, recrystallization, crystal washing with a poor solvent, and the like. These can be carried out alone or in combination.

Subsequently, a method for producing an N-alkylamine via condensation of alcohols and amines is described.

A method for producing N-alkylamines via condensation of alcohols and amines in the present invention is, for example, expressed as the following schemes (9) and (10):

[Chem. 12]

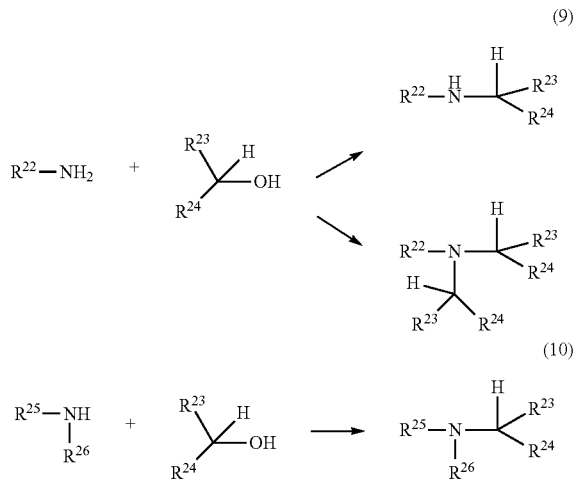

(9)

(10)

wherein $R^{22}$, $R^{25}$, and $R^{26}$, independently of one another, represent a hydrogen atom, an alkyl group, an aryl group, an aralkyl group, an alkenyl group, an alkynyl group or a heterocyclic group, preferably, represent an alkyl group or an aryl group, and more preferably, represent an aryl group, and further, among these groups, the alkyl group, the aryl group, the aralkyl group, the alkenyl group, the alkynyl group, and the heterocyclic group may have substituent(s), $R^{23}$ and $R^{24}$, independently of each other, represent a hydrogen atom, an alkyl group, an aryl group, an aralkyl group, an alkenyl group, an alkynyl group, a heterocyclic group, a halogeno group, a halogenoalkyl group or a silyl group, and more preferably, represent an alkyl group or an aralkyl group, and, among these groups, the alkyl group, the aryl group, the aralkyl group, the alkenyl group, the alkynyl group, the heterocyclic group, and the halogenoalkyl group may have substituent(s), and further, $R^{22}$ and $R^{23}$, $R^{22}$ and $R^{24}$, $R^{22}$, $R^{23}$, and $R^{24}$, or $R^{23}$ and $R^{24}$ in scheme (9) may bind to each other, and $R^{23}$ and $R^{24}$, $R^{26}$ and $R^{25}$, $R^{26}$ and $R^{24}$ and/or $R^{23}$, $R^{26}$ and $R^{25}$ and $R^{24}$ and/or $R^{23}$, or $R^{25}$ and $R^{24}$ and/or $R^{23}$ in scheme (10) may bind to each other.

In schemes (9) and (10), $R^{22}$, $R^{25}$, and $R^{26}$ are described below.

Examples of the alkyl group, the aryl group, the aralkyl group, the alkenyl group, the alkynyl group, and the heterocyclic group of $R^{22}$, $R^{25}$, and $R^{26}$ in Schemes (9) and (10) include the groups as described in detail in the description for $R^{10}$, $R^{11}$, and $R^{12}$ in schemes (1) and (2) Further, among these groups, the alkyl group, the aryl group, the aralkyl group, the alkenyl group, the alkynyl group, and the heterocyclic group may have substituent(s).

Examples of the substituents which the alkyl group, the aralkyl group, the alkenyl group or the alkynyl group may have include a heterocyclic group, a hydroxyl group, an alkoxy group, an aryloxy group, an aralkyloxy group, an amino group, a halogeno group, a silyl group, a siloxy group, an acyloxy group, and a carbonyl group having one monovalent group. Among these groups, examples of the heterocyclic group, the alkoxy group, the aryloxy group, the aralkyloxy group, the amino group, the halogeno group, the silyl group, the siloxy group, the acyloxy group, and the carbonyl group having one monovalent group include the groups as described in detail in the description for $R^{10}$, $R^{11}$, and $R^{12}$ in schemes (1) and (2).

Examples of the substituent which the aryl group or the heterocyclic group may have an alkyl group, an aryl group, an aralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group, and a carbonyl group having one monovalent group. Among these groups, examples of the alkyl group, the aryl group, the aralkyl group, the alkenyl group, the alkynyl group, the heterocyclic group, the alkoxy group, the aryloxy group, the aralkyloxy group, the amino group, the halogeno group, the halogenoalkyl group, the silyl group, the siloxy group, the acyloxy group, and the carbonyl group having one monovalent group include the groups as described in detail in the description for $R^{10}$, $R^{11}$, and $R^{12}$ in schemes (1) and (2).

Examples of the alkyl group, the aryl group, the aralkyl group, the alkenyl group, the alkynyl group, the heterocyclic group, the halogeno group, the halogenoalkyl group, and the silyl group of $R^{23}$ and $R^{24}$ in Schemes (9) and (10) include the groups as described in detail in the description for $R^{10}$, $R^{11}$, and $R^{12}$ in schemes (1) and (2) Further, among these groups, the alkyl group, the aryl group, the aralkyl group, the alkenyl group, the alkynyl group, the heterocyclic group, and the halogenoalkyl group may have substituent(s).

Examples of the substituents which the alkyl group, the aralkyl group, the alkenyl group, the alkynyl group or the halogenoalkyl group may have include a heterocyclic group, a hydroxyl group, an alkoxy group, an aryloxy group, an aralkyloxy group, an amino group, a halogeno group, a silyl group, a siloxy group, an acyloxy group, and a carbonyl group having one monovalent group. Among these groups, examples of the heterocyclic group, the alkoxy group, the aryloxy group, the aralkyloxy group, the amino group, the halogeno group, the silyl group, the siloxy group, the acyloxy group, and the carbonyl group having one monovalent group include the groups as described in the description for $R^{10}$, $R^{11}$, and $R^{12}$ in schemes (1) and (2).

Examples of the substituent which the aryl group or the heterocyclic group may have an alkyl group, an aryl group, an aralkyl group, an alkenyl group, an alkynyl group, a heterocyclic group, a hydroxyl group, an alkoxy group, an aryloxy group, an aralkyloxy group, an amino group, a halogeno group, a halogenoalkyl group, a silyl group, a siloxy group, an acyloxy group, and a carbonyl group having one monovalent group. Among these groups, examples of the alkyl group, the aryl group, the aralkyl group, the alkenyl group, the alkynyl group, the heterocyclic group, the alkoxy group, the aryloxy group, the aralkyloxy group, the amino group, the halogeno group, the halogenoalkyl group, the silyl group, the siloxy group, the acyloxy group, and the carbonyl group having one monovalent group include the groups as described in detail in the description for $R^{10}$, $R^{11}$, and $R^{12}$ in schemes (1) and (2).

When $R^{22}$ and $R^{23}$, $R^{22}$ and $R^{24}$, and $R^{22}$, $R^{23}$, and $R^{24}$ in scheme (9) bind to each other, the reaction is an intramolecular reaction and the reaction products should be cyclic compounds such as cyclic amines. Further, when $R^{23}$ and $R^{24}$ bind to each other, alcohols should be cyclic compounds such as cyclic alcohols. When $R^{23}$ and $R^{24}$ in scheme (10) bind to each other, alcohols should be cyclic compounds such as cyclic alcohols. Further, when $R^{26}$ and $R^{25}$ bind to each other, amines should be cyclic compounds such as cyclic amines. Further, when $R^{26}$ and $R^{24}$ and/or $R^{23}$, $R^{26}$, $R^{25}$ and $R^{24}$ and/or $R^{23}$, and $R^{25}$ and $R^{24}$ and/or $R^{23}$ bind to each other, the reaction is an intramolecular reaction and the reaction products should be cyclic compounds such as a cyclic amines.

In schemes (9) and (10), when $R^{22}$ to $R^{26}$, independently of each other, represent an alkenyl group or an alkynyl group, or when $R^{22}$ to $R^{26}$, independently of each other, represent an alkenyl group, an alkynyl group, an acyloxy group, and/or a carbonyl group having one monovalent group, as a substituent, these groups may be reduced in the course of the reaction.

In schemes (9) and (10), when $R^{22}$ to $R^{26}$, independently of each other, have an aralkyloxy group as a substituent, the aralkyloxy group may be reduced in the course of the reaction.

In schemes (9) to scheme (10), when $R^{22}$ to $R^{26}$, independently of each other, have a hydroxyl group as a substituent, the hydroxyl group may be oxidized in the course of the reaction.

The dehydration condensation of alcohols and amines of the present invention can be suitably carried out in the absence or presence of a solvent, but it is desirable to use a solvent. Examples of the solvent include the solvents as described in detail in dehydrogenation of alcohols, hemiacetals, and hemiaminals.

A use amount of the catalyst varies depending on a substrate, reaction conditions, the type of catalyst, and the like, but is usually in a range of 0.0001 mol % to 20 mol % (a substance amount of the ruthenium complex per a substance amount of a substrate), preferably 0.002 mol % to 10 mol %, and more preferably 0.005 mol % to 5 mol %.

Further, in the N-alkylation of the present invention, an appropriate additive may be added. Examples of the additive include the additives as described in detail in the hydrogenation of aldehydes or ketones.

It is desirable that the present reaction is carried out under an inert gas, hydrogen gas, carbon monoxide gas or the air atmosphere. Specific examples of the inert gas include argon gas and nitrogen gas. These gases and the air atmosphere may be used alone or as a mixed gas.

Since in the present reaction, dehydrogenation and hydrogenation can be carried out in the same system, a hydrogen donor is not necessarily required, but a hydrogen donor such as hydrogen gas or formic acid may be used. A pressure at which hydrogen gas is used as the hydrogen donor is usually under atmospheric pressure to 10 MPa, preferably under atmospheric pressure to 5 MPa, and more preferably under atmospheric pressure to 2 MPa. In addition, atmospheric pressure means a pressure under atmospheric pressure of hydrogen gas which does not require additional pressure of hydrogen gas.

A reaction temperature is appropriately selected in a range of usually −50° C. to 300° C., preferably 0° C. to 200° C., and more preferably 20° C. to 150° C.

A reaction time is naturally selected depending on a solvent, a reaction temperature, and other condition, but is appropriately selected in a range of usually 1 minute to 72 hours, preferably 1 minute to 24 hours, and more preferably 5 minutes to 12 hours.

The product can be subjected to post treatment, isolation, and purification, if necessary. Specific examples of a method of post-treatment include concentration, washing, extraction, back extraction, crystallization by addition of a poor solvent, and the like. These can be carried out alone or in combination. Specific examples of the method of isolation and purification include drying of a reaction solution, various chromatography, distillation, recrystallization, crystal washing with a poor solvent, and the like. These can be carried out alone or in combination.

The reaction using the ruthenium complex having the formula (1) can be all carried out while the complex is formed (in situ method). For example, the ruthenium complex having the formula (5), a primary alcohol and/or carbon monoxide, a substrate, a solvent, and, if necessary, an additive are enclosed in the same container, and hydrogenation of aldehydes, ketones, and esters can be carried out in the presence of a hydrogen donor. Examples of the solvent, the hydrogen donor, the catalytic amount, the additive, the reaction temperature, the pressure at which hydrogen gas is used, the post-treatment, the isolation, and the purification include the same conditions as solvents, hydrogen donors, a catalytic amount, additives, a reaction temperature, pressure at which hydrogen gas is used, post-treatment, isolation, and purification as described in detail in the hydrogenation of aldehydes and ketones in the above schemes (1) and (2).

Likewise, the ruthenium complex having the formula (5), a primary alcohol and/or carbon monoxide, a substrate, a solvent, and, if necessary, an additive are enclosed in the same container, whereby dehydrogenation of alcohols, hemiacetals, and hemiaminals can be carried out. Examples of the solvent, the catalytic amount, the additive, the reaction temperature, the post-treatment, the isolation, and the purification in the reaction include the same conditions as solvents, a catalytic amount, additives, a reaction temperature, pressure at which hydrogen gas is used, post-treatment, isolation, and purification as described in detail in the dehydrogenation of alcohols, hemiacetals, and hemiaminals in the above schemes (4), (5) and (6).

Further, the ruthenium complex having the formula (5), a primary alcohol and/or carbon monoxide, a substrate (amines and alcohols), a solvent, a hydrogen donor if necessary, and an additive if necessary are enclosed in the same container, whereby an N-alkylation via condensation of alcohols and amines can be carried out. Examples of the solvent, the hydrogen donor, the catalytic amount, the additive, the reaction temperature, the pressure at which hydrogen gas is used, the post-treatment, the isolation, and the purification in the reaction include the same conditions as solvents, hydrogen donors, a catalytic amount, additives, a reaction temperature, pressure at which hydrogen gas is used, post-treatment, isolation, and purification as described in detail in the N-alkylation in schemes (9) and (10).

EXAMPLES

Hereinafter, the present invention is described in detail, with reference to the Examples, but the present invention is not limited to the following Examples.

Further, in the structural formula in the Examples, geometric isomers, such as a facial/meridional isomer which a metal complex having a tridentate ligand has and a cis/trans isomer having a metal complex having a plurality of monodentate ligands are not considered.

A GC yield was determined by gas chromatography (hereinafter, referred to as GC). Apparatuses used are as follows.

Proton nuclear magnetic resonance spectrum (hereinafter, referred to as $^1$H NMR); 400 MR/DD2 (resonance frequency: 400 MHz, manufactured by Agilent Technologies, Inc.)Phosphorous 31 nuclear magnetic resonance spectrum (hereinafter, referred to as $^{31}$P NMR); 400 MR/DD2 (resonance frequency: 161 MHz, manufactured by Agilent Technologies, Inc.)

Carbon 13 nuclear magnetic resonance spectrum (hereinafter, referred to as $^{13}$C NMR): Avance III 500 (125-MHz, manufactured by Bruker Corporation)

Gas chromatography (GC); GC-4000 (manufactured by GL-SCIENCES Inc.)

DB-WAX (30 m, 0.25 mm ID, 0.25 μm df)
Inj. Temp: 200° C., Det. Temp.: 230° C.
Temp. 80° C. (0 min.) –5° C./min. –250° C. (1 min.)
HRMS; LCMS-IT-TOF (Ionization: ESI, manufactured by Shimadzu Corporation)

(Example 1) Production of Ruthenium Complex

A ruthenium complex A was prepared by the following scheme.

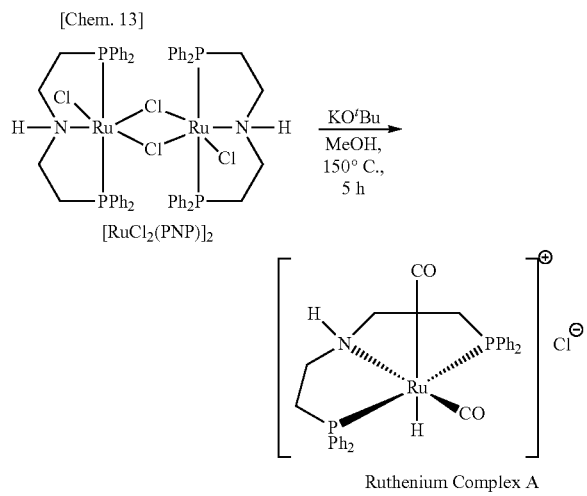

100 mg (0.16 mmol) of [RuCl$_2$(PNP)]$_2$ and 915 mg (8.2 mmol) of KO$^t$Bu were added to a 100 mL stainless steel autoclave, and after replacement with nitrogen gas, 10 mL of methanol was added. After sealing the autoclave, the reaction mixture were stirred in a bath at 150° C. for 5 hours then cooled to room temperature. 0.5 N HCl/MeOH was added to the reaction mixture until the pH range of 3 to 5, precipitated solids were separated by filtration, and the filtrate was concentrated in vacuo to give a pale yellow solid. The obtained solid was washed with 5 mL of toluene and 5 mL of water to obtain a ruthenium complex A. Further, the organic layer of the filtrate after washing was separated and concentrated in vacuo to additionally obtain the ruthenium complex A. These complexes were combined to obtain a total of 92.1 mg of the ruthenium complex A as a pale yellow solid (yield of 89%).

$^1$H NMR (400 MHz, CD$_2$Cl$_2$)
δ=8.70-8.80 (m, 1H), 8.70 (s, 1H), 7.86-7.96 (m, 4H), 7.60-7.70 (m, 4H), 7.40-7.58 (m, 12H), 3.35-3.60 (m, 2H), 3.18-3.40 (m, 2H), 2.80-2.90 (m, 2H), 2.20-2.40 (m, 2H), –6.27 (t, J=16.4 Hz)

$^{31}$P NMR (161 MHz, CD$_2$Cl$_2$): δ=57.80

$^{13}$C NMR (125 MHz, CD$_2$Cl$_2$)
δ=168.42 (S), 138.26 (S), 135.76 (t, J=23.8 Hz), 133.55 (t, J=23.8 Hz), 133.80 (t, J=6.3 Hz), 131.57 (t, J=6.3 Hz), 131.47 (S), 130.85 (S), 129.26 (t, J=5.0 Hz), 129.13 (t, J=5.0 Hz), 33.13, 33.02, 32.91, 21.43

HRMS (ESI, m/z)
Calculated value 600.078978 as C$_{30}$H$_{30}$NO$_2$P$_2$Ru([M-Cl]$^+$).
Found value 600.078160.

(Example 2) Production of Ruthenium Complex

A ruthenium complex A was prepared by the following scheme.

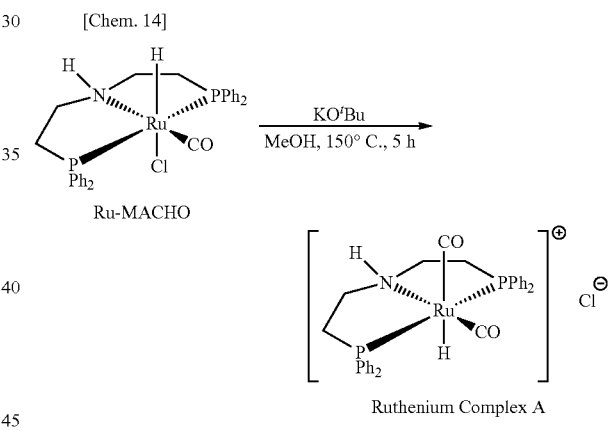

200 mg (0.33 mmol) of Ru-MACHO and 2.02 g (18.0 mmol) of KO$^t$Bu were added to a 100 mL stainless steel autoclave, and after replacement with nitrogen gas, 20 mL of methanol was added. After sealing the autoclave, the reaction mixture was stirred in a bath at 150° C. for 5 hours and cooled to room temperature. 0.5 N HCl/MeOH was added to the reaction mixture until the pH range of 3 to 5, precipitated solids were separated by filtration, and the filtrate was concentrated in vacuo to give a pale yellow solid. The obtained solid was washed with 5 mL of toluene and 5 mL of water to obtain a ruthenium complex A. Further, the organic layer of the filtrate after washing was separated and concentrated in vacuo to additionally obtain the ruthenium complex A. These complexes were combined to quantitatively obtain the ruthenium complex A as a pale yellow solid.

(Example 3) Production of Ruthenium Complex

A ruthenium complex A was prepared by the following scheme.

[Chem. 15]

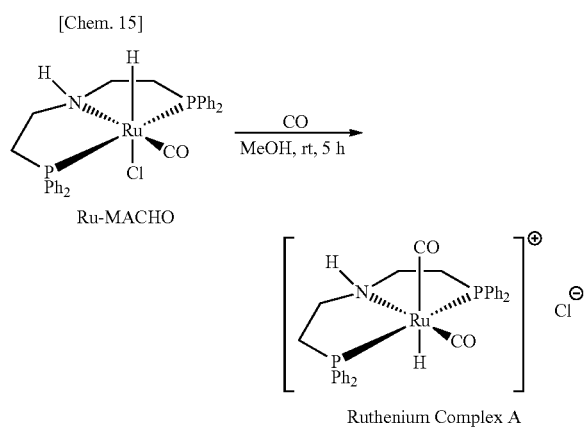

6.1 mg (0.01 mmol) of Ru-MACHO was added to a 20 mL Schlenk tube, and after replacement with nitrogen gas, 1.0 mL (1.0 mmol) of 1M NaOMe (MeOH solution) and 8.0 mL of methanol were added, and the reactants were stirred at room temperature for 10 minutes. After replacement with carbon monoxide gas, the reactants were stirred at room temperature for 1 hour, 0.5 N HCl/MeOH was added to the reaction mixture until the pH range of 3 to 5, and concentrated in vacuo. 2 mL of deuterated methylene dichloride was added to the precipitated solid and filtered. The filtrate was analyzed by 1H NMR, and conversion into the ruthenium complex A was confirmed.

(Example 4) Production of Ruthenium Complex

A ruthenium complex B was prepared by the following scheme.

[Chem. 16]

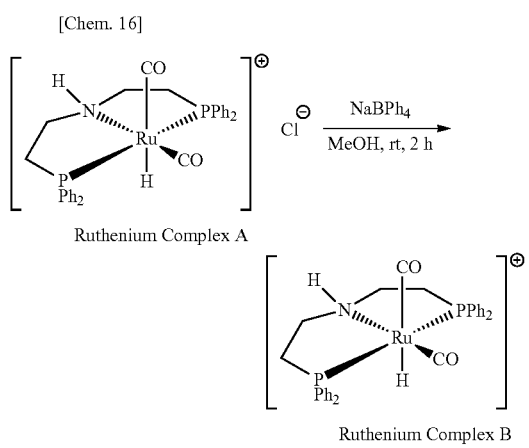

150 mg (0.24 mmol) of the ruthenium complex A and 81 mg (0.24 mmol) of NaBPh$_4$ were added to a 20 mL Schenk tube, and after replacement with nitrogen gas, 3.0 mL of methanol was added. After stirring at room temperature for 2 hours, 2 mL of water was added to the reaction mixture, and the precipitated solids were separated by filtration. The obtained solids were washed with methanol and hexane, and then concentrated in vacuo to obtain 169.9 mg of a ruthenium complex B as a white solid (yield of 77%). Single crystals of the ruthenium complex B was prepared from deuterated methylene dichloride/hexane, and the structure was determined by X-ray structural analysis.

$^1$H NMR (400 MHz, CD$_2$Cl$_2$)
δ=7.62-7.74 (m, 2H), 7.30-7.60 (m, 26H), 6.98-7.10 (m, 8H), 6.80-6.90 (m, 4H), 2.20-2.70 (m, 5H), 1.60-2.10 (m, 4H), −6.24 (t, J=16.2 Hz)
$^{31}$P NMR (161 MHz, CD$_2$Cl$_2$): δ=54.87
$^{13}$C NMR (125 MHz, CD$_2$Cl$_2$)
δ=198.72 (S), 192.53 (S), 167.99 (S), 164.59 (S), 164.20 (S), 163.81 (S), 136.33 (S), 134.41 (t, J=23.8 Hz), 133.04 (t, J=6.3 Hz), 132.69 (t, J=23.8 Hz), 131.45 (t, J=6.3 Hz), 129.68 (t, J=5.0 Hz), 129.35 (t, J=5.0 Hz), 54.16 (S), 33.14 (t, J=13.8 Hz)
Calculated value 600.078978 as C$_{30}$H$_{30}$NO$_2$P$_2$Ru([M-BPh$_4$]$^+$).
Found value 600.078086.

(Example 5) Hydrogenation of Acetophenone Using Ruthenium Complex A

[Chem. 17]

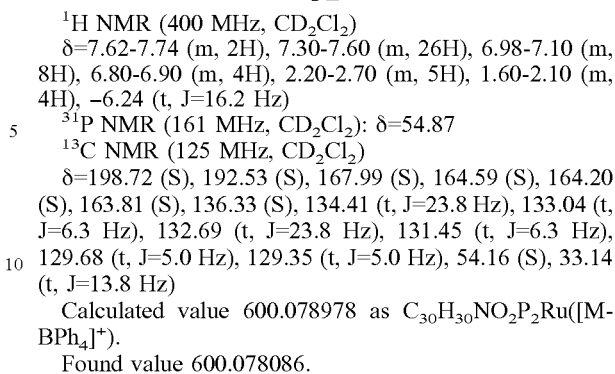

1.6 mg (0.0025 mmol) of the ruthenium complex A obtained in Example 2 was added to a 100 mL stainless steel autoclave, and after replacement with nitrogen gas, 0.25 mL (0.25 mmol) of 1 M KO$^t$Bu (THF solution), 2 mL of toluene, and 0.29 mL (2.5 mmol) of a substrate were added, and then stirred under 1 MPa of hydrogen pressure at 80° C. for 5 hours. After cooling, the reaction mixture was analyzed by GC. The GC yield of 1-phenyl-1-ethanol was 94%.

(Example 6) Hydrogenation of Methyl Benzoate Using Ruthenium Complex A

[Chem. 18]

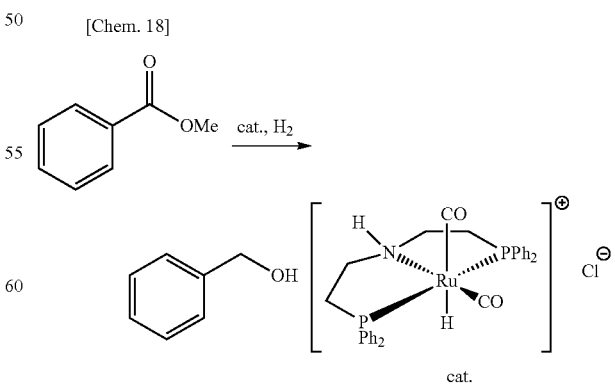

1.6 mg (0.0025 mmol) of the ruthenium complex A obtained in Example 2 was added to a 100 mL stainless steel autoclave, and after replacement with nitrogen gas, 0.25 mL (0.25 mmol) of 1 M KO$^t$Bu (THF solution), 2 mL of toluene, and 0.3 mL (2.5 mmol) of a substrate were added, and then stirred under 1 MPa of hydrogen pressure at 80° C. for 6 hours. After cooling, the reaction mixture was analyzed by GC. The GC yield of benzyl alcohol was 37%.

(Example 7) Dehydrogenation of 1-Phenyl-1-Ethanol Using Ruthenium Complex a

[Chem. 19]

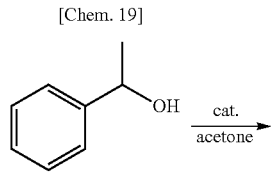
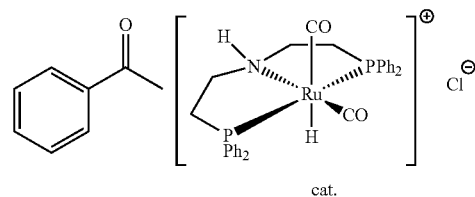

1.6 mg (0.0025 mmol) of the ruthenium complex A obtained in Example 2 was added to a 100 mL stainless steel autoclave, and after replacement with nitrogen gas, 0.25 mL (0.25 mmol) of 1 M KO$^t$Bu (THF solution), 2 mL of toluene, and 0.31 mL (2.5 mmol) of a substrate were added, and then stirred at 80° C. for 5 hours. After cooling, the reaction mixture was analyzed by GC. The GC yield of acetophenone was 67%.

(Example 8) N-Methylation of Aniline with Methanol Using Ruthenium Complex A

[Chem. 20]

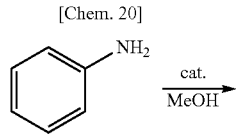
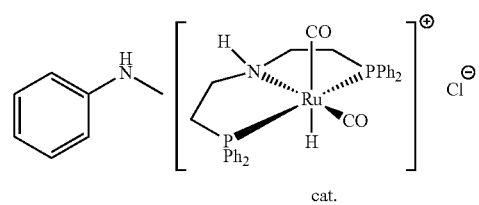

1.3 mg (0.002 mmol) of the ruthenium complex A obtained in Example 2 was added to a 100 mL stainless steel autoclave, and after replacement with nitrogen gas, 0.4 mL (0.4 mmol) of 1 M KO$^t$Bu (THF solution), 3.6 mL of methanol, and 169.5 mg (1.82 mmol) of a substrate were added, the autoclave was sealed, and the reaction mixture was stirred at 150° C. for 5 hours. After cooling, the reaction mixture was analyzed by GC. The GC yield of N-methyl aniline was 95%.

(Example 9) N-Ethylation of Aniline with Ethanol Using Ruthenium Complex A

[Chem. 21]

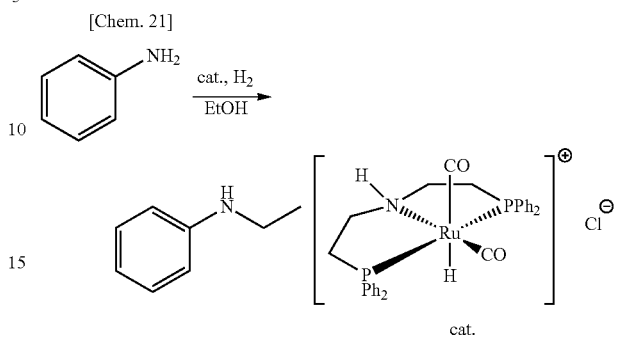

1.3 mg (0.002 mmol) of the ruthenium complex A obtained in Example 2 was added to a 100 mL stainless steel autoclave, and after replacement with nitrogen gas, 0.4 mL (0.4 mmol) of 1 M KO$^t$Bu (THF solution), 3.6 mL of ethanol, and 183.5 mg (1.97 mmol) of a substrate were added. After replacement with hydrogen gas, the reaction mixture was stirred under 1 MPa of hydrogen pressure at 150° C. for 5 hours. After cooling, the reaction mixture was analyzed by GC. The GC yield of N-ethyl aniline was 71%.

(Example 10) N-Benzylation of Aniline with Benzyl Alcohol Using Ruthenium Complex A

[Chem. 22]

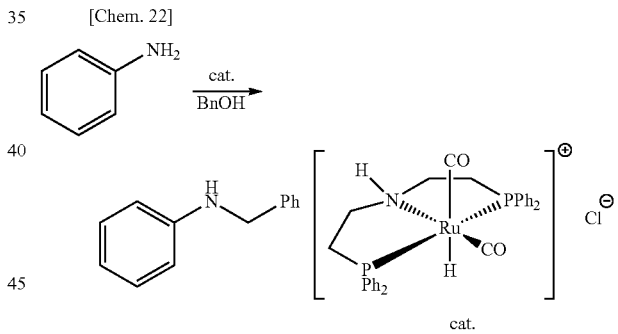

1.3 mg (0.002 mmol) of the ruthenium complex A obtained in Example 2 was added to a 100 mL stainless steel autoclave, and after replacement with nitrogen gas, 0.8 mL (0.8 mmol) of 1 M KO$^t$Bu (THF solution), 2.8 mL of tetrahydrofuran, and 191.0 mg (2.05 mmol) of a substrate were added, the autoclave was sealed, and the reaction mixture was stirred at 150° C. for 5 hours. After cooling, the reaction mixture was analyzed by GC. The GC yield of N-benzyl aniline was 92%.

INDUSTRIAL APPLICABILITY

The present invention provides a novel cationic ruthenium complex characterized by having one bis(phosphinoalkyl) amine as a tridentate ligand and two carbon monoxides as a monodentate ligand. The ruthenium complex of the present invention can be conveniently prepared from an inorganic ruthenium compound which is inexpensive and easily available. The ruthenium complex of the present invention catalyzes hydrogenation of aldehydes, ketones, and esters in the presence of a hydrogen donor. Further, the ruthenium complex of the present invention catalyzes dehydrogenation of alcohols, hemiacetals, and hemiaminals and N-alkylation via condensation of alcohols and amines. Further, the ruthenium complex of the present invention is powder which is stable in the air and easy to be handled, and thus, is suitable for industrial use. In addition, the ruthenium complex of the present invention can be performed while forming the complex, and thus, allows various reaction conditions depending on the situation. Therefore, the ruthenium complex of the present invention and the reaction using the ruthenium complex are useful in the field of organic industrial chemistry.

The invention claimed is:

1. A ruthenium complex having the following formula (1):

$$[RuX(CO)_2(PNP)]Y \qquad (1)$$

wherein X represents a hydride, Y represents a counter anion, and PNP represents a tridentate ligand having the following formula (2):

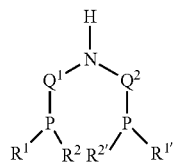

(2)

wherein in the formula (2), $R^1$, $R^2$, $R^{1'}$ and $R^{2'}$, each independently represent an optionally substituted alkyl group, an optionally substituted aryl group, an optionally substituted aralkyl group, an optionally substituted alkenyl group, an optionally substituted alkynyl group, an optionally substituted alkoxy group, an optionally substituted aryloxy group, an optionally substituted aralkyloxy group, an optionally substituted heterocyclic group or an amino group; $R^1$ and $R^2$, and $R^{1'}$ and $R^{2'}$ each independently and optionally bind to each other to form a ring with the adjacent phosphorus atom; $Q^1$ and $Q^2$ each independently represent an optionally substituted alkanediyl group or an optionally substituted aralkylene group; and CO represents carbon monoxide.

2. The ruthenium complex according to claim 1, wherein PNP represents a tridentate ligand having the following formula (3):

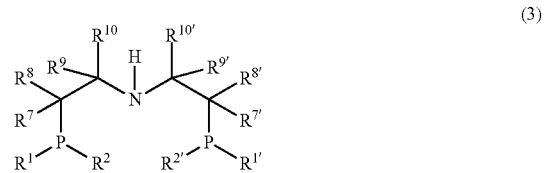

(3)

wherein in the formula (3), $R^1$, $R^2$, $R^{1'}$ and $R^{2'}$ are the groups as defined above for the formula (2); $R^7$, $R^{7'}$, $R^8$, $R^{8'}$, $R^9$, $R^{9'}$, $R^{10}$, and $R^{10'}$ each independently represent a hydrogen atom, an optionally substituted alkyl group, an optionally substituted aryl group, an optionally substituted aralkyl group, an optionally substituted alkenyl group, an optionally substituted alkynyl group, an optionally substituted alkoxy group, an optionally substituted aryloxy group, an optionally substituted aralkyloxy group, an optionally substituted heterocyclic group or an amino group; $R^7$ and $R^8$ or $R^9$ or $R^{10}$, $R^{7'}$ and $R^{8'}$ or $R^{9'}$ or $R^{10'}$, $R^8$ and $R^9$ or $R^{10}$, $R^{8'}$ and $R^{9'}$ or $R^{10'}$, $R^9$ and $R^{10}$ or $R^{9'}$ or $R^{10'}$, $R^{9'}$ and $R^{10}$ or $R^{10'}$, and $R^{10}$ and $R^{10'}$ each independently and optionally bind to each other to form a ring with the adjacent carbon atom(s).

3. The ruthenium complex according to claim 1, wherein PNP represents a tridentate ligand having the following formula (4):

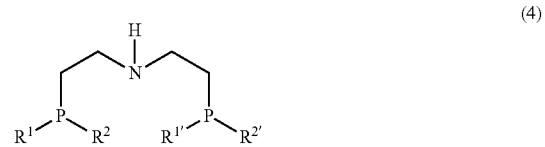

(4)

wherein in the formula (4), $R^1$, $R^2$, $R^{1'}$ and $R^{2'}$ are the groups as defined above for the formula (2).

4. The ruthenium complex according to claim 3, wherein $R^1$, $R^2$, $R^{1'}$ and $R^{2'}$ each independently represent an optionally substituted alkyl group or an optionally substituted aryl group.

5. A method for producing alcohols, aldehydes or hemiacetals by hydrogenation of esters in the presence of the ruthenium complex according to claim 1 as a catalyst.

* * * * *